United States Patent [19]
Matthews et al.

[11] Patent Number: 5,858,749
[45] Date of Patent: Jan. 12, 1999

[54] **BIFUNCTIONAL PROTEIN FROM CARROTS (*DAUCUS CAROTA*) WITH ASPARTOKINASE AND HOMOSERINE DEHYDROGENASE ACTIVITIES**

[75] Inventors: Benjamin F. Matthews, Laurel; Jane M. Weisemann, Brunswick, both of Md.

[73] Assignee: The United States of America as represented by the Secretary of Agriculture, Washington, D.C.

[21] Appl. No.: 380,182

[22] Filed: Jan. 24, 1995

Related U.S. Application Data

[62] Division of Ser. No. 746,705, Aug. 16, 1991, Pat. No. 5,451,516.

[51] Int. Cl.⁶ .............................. C12N 9/04; C12N 9/00; C12N 9/12
[52] U.S. Cl. .......................... 435/190; 435/183; 435/194
[58] Field of Search .................................... 435/183, 190, 435/194, 212

[56] References Cited

U.S. PATENT DOCUMENTS 5,451,516  9/1995  Matthews et al. ...................... 435/190

OTHER PUBLICATIONS

Matthews et al. (May, 1991) *Plant Physiol.*, 96(1), "Cloning an mRNA Encoding the Bifunctional Enzyme Aspartokinase–Homoserine Dehydrogenase from Carrot", (Suppl. p. 126), Abstr. No. 847.

Wilson et al. (1991) *Plant Physiol.*, 97(4), "Bifunctional Protein in Carrot Contains Both Aspartokinase and Homoserine Dehydrogenase Activies", pp. 1323–1328.

Aarnes et al. (1974) *Phytochemistry*, 13(12), "Threonine–Sensitive Aspartate Kinase and Homoserine Dehydrogenase from *Pisum sativum*", pp. 2717–2724, in *Chem. Abstr.*, 82, p. 178, Abstr. No. 108,005.

Azevedo et al. (1992) *Phytochemistry*, 31(11), "Aspartate Kinase Regulation in Maize: Evidence for Co–Purification of Threonine–Sensitive Aspartate Kinase and Homoserine Dehydrogenase", pp. 3731–3734.

Muehlbauer et al. (1994) *Plant Physiol.*, 106(4), "Molecular Genetics of the Maize (*Zea mays L.*) Aspartate Kinase–Homoserine Dehydrogenase Gene Family", pp. 1303–1312.

Ghislain et al. (1994) *Plant Mol. Biol.*, 24(6) "Molecular Analysis of the Aspartate Kinase–Homoserine Dehydrogenase Gene from *Arabidopsis thaliania*", pp. 835–851, in *Chem. Abstr.*, 121(15), p. 273, Abstr. No. 171,793.

Dotson et al., *Plant Physiol.*, vol. 93, pp. 98–104 (1990).

Turano et al., *Plant Physiol.*, vol. 92, pp. 395–400 (1990).

Dotson et al., *Plant Physiol.*, vol. 91, pp. 1602–1608 (1989).

Matthews et al., *Plant Physiol.*, vol. 91, pp. 1569–1574 (1989).

Krishnaswamy et al., *Archives of Biochemistry and Biophysics*, vol. 227(1), pp. 210–224 (Nov., 1983).

Krishnaswamy et al., *Archives of Biochemistry and Biophysics*, vol. 222(2), pp. 449–463 (15 Apr. 1983).

Matthews et al., *Z. Pflanzenphysiol.*, vol. 96(5), pp. 453–463 (1980).

Walter et al., *The Journal of Biological Chemistry*, vol. 254(4) pp. 1349–1355 (25 Feb. 1979).

Matthews et al., *Canadian Journal of Botany*, vol. 57(4), pp. 299–304 (15 Feb. 1979).

Matthews et al., *Z. Naturforsch*, vol. 34, pp. 1177–1185 (1979).

Matthews et al., *Phytochemistry*, vol. 18, pp. 395–400 (1979).

Matthews et al., *Planta*, vol. 141, pp. 315–321 (1978).

Bryan et al., *Plant Physiol.*, vol. 59, pp. 673–679 (1977).

Matthews et al., *Plant Physiol.*, vol. 55, pp. 991–998 (1975).

*Primary Examiner*—Jon P. Weber
*Attorney, Agent, or Firm*—M. Howard Silverstein; John Fado; Janelle S. Graeter

[57] ABSTRACT

A bifunctional enzyme has been isolated and purified from carrots which has both aspartokinase and homoserine dehydrogenase activities in the same polypeptide. The enzyme can be used to regulate lysine, homoserine, threonine, isoleucine and methionine content in plants. The DNA sequence encoding the bifunctional enzyme is also disclosed.

5 Claims, 24 Drawing Sheets

| Fig. 8A |
| Fig. 8B |
| Fig. 8C |
| Fig. 8D |
| Fig. 8E |
| Fig. 8F |

Fig. 8

```
1
G   GAG  TCG  TCG  AAG  TTT  TAC  ATT  GCT  TCC  GTT  ACA  ACT  GCA  GTT  CCT  TCT
    E    S    S    K    F    Y    I    A    S    V    T    T    A    V    P    S
                                                                         50

CTC  GAT  TCC  GTT  GAG  AAG  GTT  CAC  CTT  CCC  AGG  GGT  GCT  ATG  TGG  TCT  ATT  CAT
L    D    S    V    E    K    V    H    L    P    R    G    A    M    W    S    I    H
                                              150                100

AAA  TTT  GGA  GGC  ACC  TGT  GTG  GGA  AGC  TCT  GAA  AGG  ATC  CGA  AAT  GTT  GCA  GAG  ATA
K    F    G    G    T    C    V    G    S    S    E    R    I    R    N    V    A    E    I
                                                      200

GTT  GTG  GAG  GAT  TCT  GAA  AGA  AAG  CTA  GTT  GTA  TCT  GCA  ATG  TCA  AAG  GTC
V    V    E    D    S    E    R    K    L    V    V    S    A    M    S    K    V
                              250

ACA  GAT  ATG  TAT  GAT  CTA  ATT  TAC  AAG  CAC  TTA  ACA  GCA  GAT  TCT  CTC  TTA  GAT
T    D    M    Y    D    L    I    Y    K    H    L    T    A    D    S    L    L    D
                        300

TCT  GCG  GAT  CTC  GTT  ATG  GAA  AAG  CTG  CAG  GCC  GAA  TTT  GAT  AAT  AAC  CTC  AAA
S    A    D    L    V    M    E    K    L    Q    A    E    F    D    N    N    L    K
     350                                                                            450

GGA  GAT  GAC  CTT  AGA  TTT  TAC  ATA  GCT  GGT  CAT  ACC  TTT  TCG  ATA  AGA  AAG  GAT  TTT
G    D    D    L    R    F    Y    I    A    G    H    T    F    S    I    R    K    D    F
                                                                    500

GCA  ATG  CGT  GCA  GGA  GAG  CTA  TAC  CAG  CTG  TCA  GCT  CAG  CTG  TTG  TCA  TTT  GTA  GTA
A    M    R    A    G    E    L    Y    Q    L    S    A    Q    L    L    S    F    V    V
400                                                              550

GTT  GTG  GGA  CAT  GGA  GAG  CTA  TGG  TCA  GCT  CAG  CTG  TTG  TCA  TTT  GTA  GTA
V    V    G    H    G    E    L    W    S    A    Q    L    L    S    F    V    V

AAT  GGG  GGT  GAC  TGT  AAT  TGG  ATG  GAC  ACA  CGA  GAT  GTT  CTT  GTT  AAT  CCT  GCT
N    G    G    D    C    N    W    M    D    T    R    D    V    L    V    N    P    A
```

```
GGA TCT AAT CAA GTC GAT CCT GAT TAT TTG GAA TCT GAG AAG AGA CTT GAG AAA TGG
 G   S   N   Q   V   D   P   D   Y   L   E   S   E   K   R   L   E   K   W
                         600             650

TTC TCC AGC AAC CAG TGT CAG ACA ATT GTT GCG ACA GGT TTT ATA AGC ACG CCT
 F   S   S   N   Q   C   Q   T   I   V   A   T   G   F   I   S   T   P
                     700

CAA AAT ATA CCT ACA ACT TTG AAA AGA GAC GGA AGT GAC TTT GCT GCC ATA ATG
 Q   N   I   P   T   T   L   K   R   D   G   S   D   F   A   A   I   M
             750

GGT GCT TTA AGG GCT GGT CAA GTC ACG ATT TGG ACT GAT TTT TCT GCC AAT GGT TAT
 G   A   L   R   A   G   Q   V   T   I   W   T   D   F   S   A   N   G   Y
     800                                                             850

AGT GCA GAT CCT CGA AAA GTT AGT GAG GCT GTG GTA TTA AAG CCC TTA CGT ACT CAA
 S   A   D   P   R   K   V   S   E   A   V   V   L   K   P   L   R   T   Q
                                                     PEP.76

GAA GCC TGG GAG ATG TCA TAT TTT GGG GCT AAT GTG CAT TTA AAT ATA ACT ATC ATT
 E   A   W   E   M   S   Y   F   G   A   N   V   H   L   N   I   T   I   I
                         900                     950

CCT GTG ATG CGA TAT GAC ATT CCA ATT GTA ATA AGA TTC AAC CTA TCT GCT AAA TTG
 P   V   M   R   Y   D   I   P   I   V   I   R   F   N   L   S   A   K   L
                                     1000

CCG GGA ACA ATG ATA TGC CGA GAA TCT GTA GGC GAA ACT GAA GAT GGG TTA AAA TTG
 P   G   T   M   I   C   R   E   S   V   G   E   T   E   D   G   L   K   L
```

```
GAA TCT CAT GTC AAA GGA TTT GCT ACT ATT GAT AAT CTG GCG CTC ATT AAT GTT GAA
 E   S   H   V   K   G   F   A   T   I   D   N   L   A   L   I   N   V   E
             PEP.90                     1050

GGA ACT GGA ATG GCT GGT CCT GTT ACA GCT AGT GCA ATT TTT GGT GCT GTC AAG
 G   T   G   M   A   G   P   V   T   A   S   A   I   F   G   A   V   K
             1100                1150                    [S]

GAT GTG GGA GCT AAT GTT ATA ATG TCT CAG GCT AGC AGT GAG CAT TCT ATT TGC
 D   V   G   A   N   V   I   M   S   Q   A   S   S   E   H   S   I   C
         1200                                                        1250

TTT GCT GTG CCT GAG TTA GAT ACA GTT AAA GCT GTT GCT AAA GCT TTG GAG GCC AGA TTT
 F   A   V   P   E   L   D   T   V   K   A   V   A   K   A   L   E   A   R   F

CGT CAA GCT CTT GAT GCA ACA GTT GCA GGC CAA AAG ATG ATA TCT CCA AAC TGT AGC CTT
 R   Q   A   L   D   A   T   V   A   G   Q   K   M   I   S   P   N   C   S   L
                                                            1300

ATC TTG GCA GCG CTT GCA ACT GTA GCT GCA AAG GCC AAT ATA AAC GTT ACT CCT GCT ATA GCC CAG GGC TGT ACA
 I   L   A   A   L   A   T   V   A   A   K   A   N   I   N   V   T   P   A   I   A   Q   G   C   T
                                                    1350                 1400

TTC AAT TAT ACT GTA GTT CTC AGT CGA GAA GAT TGT GTG AGG GCT TTG AAA GCT
 F   N   Y   T   V   V   L   S   R   E   D   C   V   R   A   L   K   A
             1450                                1500

GAG TAT ATC ACT GTA TTT TAT CTG TCG AGA ACC ACA ATA GCA GTG GGT ATT GTC GGA CCT
 E   Y   I   T   V   F   Y   L   S   R   T   T   I   A   V   G   I   V   G   P

GTC CAT TCA AGA
 V   H   S   R
```

Fig. 8C

```
GGA TTA ATC GGA GCT ACT TTA CTT GAC CAG AGG GAT CAG CTC GCA ATC CTC AAG
 G   L   I   G   A   T   L   L   D   Q   R   D   Q   L   A   I   L   K
             1550                                                1650
GAA AAT TCT AAA ATT GAT TTG CGT GTT ATG GGT ATC ACC GGA TCG AGA ACA ATG CTT
 E   N   S   K   I   D   L   R   V   M   G   I   T   G   S   R   T   M   L
     1600                                                    1700
CTG AGC GAA ACG GGA ATC GAT TTA AGT AGA TGG AGA GAA GTC CAA AAA GAG AAA GGG
 L   S   E   T   G   I   D   L   S   R   W   R   E   V   Q   K   E   K   G
                                             1750
CAA ACA GCT GTT GGC CTA GAA TTT GTA CAA CAT GTG CGT GGA AAT TTT CAT ATT CCA
 Q   T   A   V   G   L   E   F   V   Q   H   V   R   G   N   F   H   I   P
                                     1800
AGC ACT GTT ATA GAT GTA AAA TGT ACA GCA GAC TCT ATT GAA GTG GCA TAC CAT GAC
 S   T   V   I   D   V   K   C   T   A   D   S   I   E   V   A   Y   H   D
                                         1850
TGG TTG TGT AGG GGA ATT TTG AAG TTG AGA GCT CTC CAG CGG CGA TCC TAT TCA CCC
 W   L   C   R   G   I   L   K   L   R   A   L   Q   R   R   S   Y   S   P
                                                 PEP. 97
CTT GAT CAG TAT TTG AAG GGA ATT GTC CAC GCT GGT CCG ATC CTC CAG ATA ACC TTC
 L   D   Q   Y   L   K   G   I   V   H   A   G   P   I   L   Q   I   T   F
                                     1900
TAT GAA GCT GTT ACT GTT GGT GCT CTC GGT CTC CCG ATC ACC ACT TTG CAG GGA CTT
 Y   E   A   V   T   V   G   A   L   G   L   P   I   T   T   L   Q   G   L
             1950
 Y   E   A   V   T   V   G   A   L   G   L   P   I   T   T   L   Q   G   L
```

Fig. 8D

```
GAA ACC GGG GAC AAG ATA TTG CGA ATT GAA GGC ATT TTC AGT GGG ACT CTT AGT TAC
 E   T   G   D   K   I   L   R   I   E   G   I   F   S   G   T   L   S   Y
             2000                                                      2050

ATA TTC AAC AAC TTT AAG AGT ACA CCT TTT AGT GAA GTG GTA AGT GAA GCA AAA
 I   F   N   N   F   K   S   T   P   F   S   E   V   V   S   E   A   K
                                 2100

GCG GCA GGG TAT ACT GAA CCA GAT CCA AGG GAT CTA GAT GCC GGA ACT GAT GTT GCT
 A   A   G   Y   T   E   P   D   P   R   D   L   D   A   G   T   D   V   A
                                             2150

AGA AAG GTA ATA ATT CTT GCT AGA GAA TCT GGA TTA AAG CTC GAA CTG TCT GAT ATC
 R   K   V   I   I   L   A   R   E   S   G   L   K   L   E   L   S   D   I
                                                     2200

CCT GTA CAG AGC CTT GTT CCA CAG TTT CCA CTA AGG GGT ATT GCG TCA GCC GAA GAA TTT
 P   V   Q   S   L   V   P   Q   F   P   L   R   G   I   A   S   A   E   E   F
                                                 2250

CTG CTA CAG GGA GAA GTT CTA CCA CAG TTT GAT TCA GAT ATG ACC AGA AAA CGA GAG AAT
 L   L   Q   G   E   V   L   P   Q   F   D   S   D   M   T   R   K   R   E   N
                                                         2300

AAT GCA GGG GAA TTG AAA GTT CTA AGG TAC GTT GGG GTG GAT GCC GTA AAT CAA AAA GGT
 N   A   G   E   L   K   V   L   R   Y   V   G   V   D   A   V   N   Q   K   G
                                     2350

GTT GTT GAA TTG AAA AGA TAC AAG CAG CAC CCG TTC GCA CAG CTT TCT GGG TCC
 V   V   E   L   K   R   Y   K   Q   H   P   F   A   Q   L   S   G   S
                 2400
```

```
2450
GAT AAC ATC ATT GCT TTC ACA ACT GAA AGA TAC AAC AAG CAA CCT CTT ATA ATT CGA
 D   N   I   I   A   F   T   T   E   R   Y   N   K   Q   P   L   I   I   R
                                                          2500
                                                2550
GGT CCT GGT GCT GGG GCA GAG GTG ACA GTG GGA GTA TTC AGT GAT ATT TTG CGG
 G   P   G   A   G   A   E   V   T   V   G   V   F   S   D   I   L   R
                                    2600

CTT GCT TCA TAT CTT GGT GCA CCA TCA TAA  TCCATTAGTTGAGCTCTCAATGTTTTACCCTTTGT
 L   A   S   Y   L   G   A   P   S   *
PEP.33  A   S   Y   L   G   A   P   S
                        2650
                                                                    2700
CAGCCCAAATTATGTTATAGAATTTAGGGAGCTTTTGCCTATTATTAGGTTAGTATCAAACATTCTTCTACGCT
                                            2750
GCATAAGAGAACACTTCATGCAATTTGGGTTTCTTTAGTGGCTTTCTAGCCAACCCAAATGTGTCATAGTCTCCA
                2800                                                     2850
CGATGCAGAGTTGATAGAATTGTTACAAGGGGATGTATTATAGAACCAAGCCAATTAAACGGTGTATCCTTATTT
                                        2900
GGTAAGGGATAACGTATTAATAATGCCAAAGTGTGTAACATCTTTTGTTGCGAATAAATTT
```

| Fig. 9A |
|---------|
| Fig. 9B |
| Fig. 9C |

Fig. 9

```
Carrot   1  ESSSKFYIAASVTTAVPSLDDSVEKVHLPRGAMWSIHKFGGTCVGSSERI          50
            |::  ::||:::::::
E.coli   1  ..............................MR.VLKFGGTSVANAERF          17
                                            *****

51  RNVAEIVVEDDSERKL.VVVSAMSKVTDMMYDLIYKAQSRDDSYESALDA          99
            .|:|.:::::.|:||: .||:.|:|::::::.|||..:|.::.:.|:.|
        18  LRVADILESNARQGQVATVLSAPAKITNHLVAMIEKTISGQDALPNISDA          67
                          *

100  VME.KHKLTAFDLLDGD.DLARFLTRLQHDVNNLKAMLRAIYIAGHATES         147
            :|: ||:||.::|.|:| :|:|.||:|::|.::|:.:|||:::::::.::
        68  ERIFAELLTGLAAAQPGFPLAQLKTFVDQEFAQIKHVLHGISLLGQCPDS         117
                  *

148  FSDFVVGHGELWSAQLLSFVIRKNGGDCNWMDTRDVLVVNPAGSNQVDPD         197
            :::|:::|:|::|  |:    |: :              .:  :.:::.
       118  INAALICRGEKMSIAIMAGVLEARG..........HNVTVIDPVEKLLAVGH       159
                  *

198  YLESEKRLE...KWFSSNQCQT...IVATGFIASTPQNIPTTLKRDGSDF         241
            ||||| |:|   .::.: .:.   |:|: :||: ::: : :|::::|.:
       160  YLESTVDIAESTRRIAASRIPADHMVLMAGFTAGNEKGELVVLGRNGSDY         209
               *                                           *

242  SAAIMGALLRAGQVTIWTDVNGVYSADPRKVSEAVVLKTLSYQEAWEMSY         291
            |||::.||||| |||:|||||||||:..|| | |.:|||:|::||||:|
       210  SAAVLAACLRADCCEIWTDVNGVYTCDPRQVPDARLLKSMSYQEAMELSY         259
                *                               *
```

Fig. 9A

```
292 FGANVLHPRTIIPVMRYDIPIVIRNIFNLSAPGTMICRESVGETEDGLKL 341
        ||||||||||| ::   . ::::: :   | |||||    ::  ||
260 FGAKVLHPRTITPIAQFQIPCLIKNTGNPQAPGTLI...GASRDEDEL.. 304
        *                                           *

342 ESHVKGFATIDNLALINVEGTGMAGVPGTASAIFGAVKDVGANVIMISQA 391
      :|| :| ||:  :::: | |  ||||:||:  | ||:|||:|::| :
305 ..PVKGISNLNNMAMFSVSGPGMKGMVGMAAARVFAAMSRARISVVLITQS 352

392 SSEHSICFAVPESEVKAVAKALEARFRQALDAGRLSQVAIIPNCSILATV 441
    ||| ||  | |:  :|  ::| ||  |::: | ||| :|  | .||::|
353 SSEYSISFCVPQSDCVRAERAMLEEFYLELKEGLLEPLAVAERLAIISVV 402

442 GQKMASTPGVSATLFNALAKANINVRAIAQGCTEYNITVVLSREDCVRAL 491
    |:  ::||:||  ||:|:|| ||||:||:||:|:   |:|:|  |:  |
403 GDGLRTLRGISAKFFAALARANININIVAIAQGSSERSISVVVNNDDATTGV 452

492 KAVHSRFYLSRTTIAVGIVGPGLIGATLLDQLRDQAAILKENSKIDLRVM 541
    | :| |    |    | : |  ||  ||:|::|:  | ||: ::|||| 
                                          °
453 RVTHQMLFNTDQVIEVFVIGVGGVGGALLEQLKRQQSWLK.NKHIDLRVC 501

542 GITGSRTMLLSETGIDLSRWREVQKEKGQTAGLEKFVQHVRGNHFIPSTV 591
    |:  : :: |:: :: ::     ::|::|| | |:| |:|:: : ::: 
502 GVANSKALLTNVHGLNLENWQEELAQAKEPFNLGRLIRLVKEYHLL.NPV 550

Fig. 9B
```

```
592  IVDCTADSEVASHYHDWLCRGIHVITPNKKANSGPLDQYLKLRALQRRSY  641
     |::|||||::|||||:|:|||||||||:|||||:||:||||||.||||
551  IVNCTSSQAVADQYADFLREGFHVVTPNKKANTSSMDYYHQLRYAAEKSR  600
               o    o                      o

642  THYFYEATVGAGLPIITTLQGLLETGDKILRIEGIFSGTLSYIFNNFKST  691
     |:||||:|||||||||:||||||||:|:|:||||:|||:|||||:::::
601  RKFLYDINVGAGLPVIENLQNLLNAGDELMKFSGILSGSLSYIFGKLDEG  650
                          o                    oo

692  TPFSEVVSEAKAAGYTEPDPRDDLAGTDVARKVIILARESGLKLELSDIP  741
     |.||||:|||||:|||||||||||||:|||||||||||||:|||:|||
651  MSFSEATRLAREMGYTEPDPRDDLSGMDVARKLLILARETGRELELADIE  700
      o          o          o  o          o  ooo 742  VQSLVPEPLRGIASAEEFLLQLPQFDSDMTRKREDAENAGEVLRYVGVVD  791
     :: |:|||||||::|||:|||::|||::|||||:|||:|||||||||:|
701  IEPVLPAEFNAEGDVAAFMANLSQLDDLFAARVAKARDEGKVLRYVGNID  750
      o   o  o  o  o  o     o  o    o    o         o 792  AVNQKGVVELKRYKKEHPFAQLSGSDNIIAFTTERYNKQPLIIRGPGAGA  841
     |:::| ||||||:|:|:|||::|||:||||:|||:|:||||:|||||||
751  E.DGVCRVKIAEVDGNDPLFKVKNGENALAFYSHYYQPLPLVLRGYGAGN  799
      o  o          o  o                    ooo 842  EVTAGGVFSDILRLASY.LGAPS* 864
     :|||||||:|:||||:|.|:||
800  DVTAAGVFADLLRTLSWKLGV... 820
      oo     o     o
```

Fig. 9C

BIFUNCTIONAL PROTEIN FROM CARROTS (*DAUCUS CAROTA*) WITH ASPARTOKINASE AND HOMOSERINE DEHYDROGENASE ACTIVITIES

This is a division, of application Ser. No. 07/746,705 filed Aug. 16, 1991 now U.S. Pat. No. 5,451,516.

BACKGROUND OF THE INVENTION

1. Field of the Invention

The present invention relates to an isolated and purified bifunctional protein from carrots (*Daucus carota* L. cv Danvers) with aspartokinase and homoserine dehydrogenase activities. The invention further relates to a nucleic acid fragment encoding a bifunctional protein with aspartokinase and homoserine dehydrogenase activities.

2. Description of the Background Art

Plants can convert asparate to the amino acids methionine, threonine, lysine and isoleucine (J. Bryan, *Biochemistry of Plants*, (B. Miflin ed.) Academic Press, New York, pp. 403–452 (1980)). As these amino acids are essential in the diets of many animals, there is much interest in understanding the control mechanisms that determine the quantity of these essential amino acids in food sources. Enzymes control the pathways leading to the synthesis of the essential amino acids methionine, threonine, lysine and isoleucine. The isolation of clones of the enzyme genes from plants would enable one to determine the relationship between various forms of the enzymes, the number of genes involved, and the regulation of the pathway. Knowledge gained from the study of the amino acid pathway genes would allow the engineering of the pathway to alter the amino acid pool composition of plants used as protein sources.

Aspartokinase (AK.2) (E.C. 2.7.2.4) and homoserine dehydrogenase (HSDH) (E.C.1.1.1.3) catalyze steps in the pathway for the synthesis of lysine, methionine, and threonine from aspartate. AK.2 catalyzes the phosphorylation of aspartate to β-aspartyl phosphate. It is the first enzyme of the pathway leading to the synthesis of the essential amino acids lysine, threonine, methionine and isoleucine in plants. β-aspartyl phosphate is converted to aspartate semialdehyde, which can either be used to make lysine or it can be reduced by the enzyme homoserine dehydrogenase (HSDH) to homoserine. Through further enzymatic steps homoserine is converted first to phosphohomoserine and eventually to threonine and isoleucine or methionine.

In higher plants there are commonly at least two forms of AK which are differentially feedback inhibited by the end products lysine and threonine (See H. Davies et al., *Plant Physiol* 62: 536–541 (1978); B. Matthews et al., *Planta* 141: 315–321 (1978); B. Matthews et al., *Z Naturforsch* 346: 1177–1185 (1979); B. Matthews et al., *Z Pflanzenphysiol* 96: 453–463 (1980) and K. Sakano et al., *Plant Physiol* 61: 115–118 (1978)). HSDH.2 (EC 1.1.1.3) catalyzes the reversible conversion of aspartate semialdehyde to homoserine and is at the branch point leading to threonine, methionine and isoleucine synthesis.

Regulation of carrot (*Daucus carota*) AK and HSDH activities from roots and cell suspension cultures has been studied extensively (See H. Davies, supra; B. Matthews (1978, 1979, 1980) supra; J. Relton et al., *Biochim Biophys Acta* 953: 48–60 (1988); K. Sakano *Plant Physiol* 63: 583–585 (1979); and K. Sakano, supra). HSDH has been purified to apparent homogeneity and characterized (B. Matthews et al., *Plant Physiol* 91: 1569–1574 (1989)). Two forms of HSDH have been identified in vitro: one sensitive to threonine inhibition and one insensitive. Carrot HSDH activity reversibility converts between a threonine-insensitive form in the presence of K+ and a threonine-sensitive form in the presence of threonine which possess distinctly different electrophoretic mobilities on PAGE gels stained for enzymatic activity. Three forms of aspartate kinase have been isolated from carrot: form I is strongly inhibited by lysine, form II is strongly inhibited by threonine, and form III is partially inhibited by both. The relationship between these three forms is not yet defined. Antibody to this HSDH has been examined for specificity and cross reactivity with soybean and *E. coli* (F. Turano et al., *Plant Physiol* 92: 395–400 (1990)).

These biosynthetic pathways in plants are similar to pathways found in bacteria (G. Cohen et al., *Cellular and Molecular Biology* (F. Neidhardt ed.) American Society for Microbiology, Washington, D.C., pp. 429–444 (1987); and G. Cohen, *Amino Acids: Biosynthesis and Genetic Regulation* (K. Hermann and R. Somerville, eds.) Addison-Wesley, Reading, pp. 147–171 (1983)). Many of the bacterial genes that code for the enzymes of the aspartate pathway have been cloned and sequenced (G. Cohen (1987), supra). Only one of the plant genes in this pathway has been isolated (dihydrodipicolinate synthase (T. Kaneko, *J Biol Chem* 265: 17451–55 (1990)), which catalyzes the first reaction specific to lysine synthesis).

In *E. coli* there are three genes coding for aspartate kinase and/or homoserine dehydrogenase. One, lysC, codes for a lysine-sensitive aspartate kinase (AKIII), is regulated by lysine and does not contain HSDH activity. The other two genes code for bifunctional AK-HSDH proteins (G. Cohen (1983), supra). ThrA is repressed by threonine and isoleucine and the enzymatic activity of AKI-HSDHI is inhibited by threonine. MetL is repressed by methionine, but the protein AKII-HSDHII is not responsive to end product inhibition. It is not known if the multiple enzyme forms in plants are encoded by separate genes or if these genes are subject to transcriptional or translational regulation.

In *Bacillus subtilis* (R. Bondaryk et al., *J Biol Chem* 10: 585–591 (1985); and N. Chen et al., *J Biol Chem* 262: 8787–8798 (1987)), *Brevibacterium lactofermentum* (Mateos et al., *Nucleic Acids Research* 15: 10598 (1987)), *Rhodospirillum rubrum* (P. Datta *J Biol Chem* 245: 5779–5787 (1970)) and *Saccharomyces cerevisiae* (J. Rafalski et al., *J Biol Chem* 263: 2146–2151 (1988)) HSDH and AK activities reside on separate proteins encoded by separate genes.

Enzymes involved in the synthesis of the aspartate family of amino acids appear to be relatively low in abundance. Homoserine dehydrogenase has been purified to homogeneity from maize (T. Walter et al., *J Biol Chem* 254: 1349–1355 (1979)) and carrot (B. Matthews (1989), supra), while aspartokinase has been purified to homogeneity from maize (S. Dotson et al., *Plant Physiol* 91: 1602–1608 (1989)) and partially purified from carrot (B. Matthews (1978, 1979), supra). There have been no indications in the literature that these two enzyme functions reside on the same protein in plants. In most of the plant species studied multiple forms of AK and HSDH have been identified in vitro (J. Bryan, supra). These forms are distinguished by their sensitivity to feedback inhibition (in particular by threonine and lysine) and by their molecular weight and subunit composition. Because there are AK activities sensitive to lysine and threonine but HSDH activity is sensitive only to threonine, a common peptide was not suspected. Although HSDH activity is associated with both lysine- and threonine-sensitive AK, the ratio of activities is variable for reasons unknown at this time. In E. coli AKI-HSDHI both enzymatic activities are inhibited by threonine. The E. coli AKIII is inhibited by lysine or threonine. Because of these E. coli examples, an aspartokinase sensitive to lysine and associated with threonine-sensitive homoserine dehydrogenase appears to be inconsistent.

Other factors have prevented detection of these coincident activities. It has been observed that both AK and HSDH eluted off the gel filtration column at the same location but it was assumed that it was a simple case of coelution of two large, similarly-sized proteins. The purification protocol (Matthews (1989), supra) for HSDH had already been established before the protocol for AK. In the protocol for purification of HSDH from carrot suspension culture cells (Matthews (1989), supra), a heat denaturation step is utilized and activity of AK is lost after the heat denaturation step. Even though AK activity of the E. coli bifunctional AKI-HSDHI is lost after heating, the comparison was not made because a bifunctional protein in plants was not suspected.

Furthermore, in contrast to E. coli, not all bacteria have bifunctional AK-HSDHs. In Brevibacterium lactofermentum separate genes encode separate AK and HSDH proteins. The B. subtilis gene possesses two initiation sites to produce AKI and a truncated, but functional AKII protein (N. Chen, supra). In yeast, a gene encoding AK also has been identified (J. Rafalski, supra); this gene does not appear to encode HSDH. HSDH has been extensively examined in Rhodospirillum rubrum (P. Datta et al., J Biol Chem 240: 3023–3033 (1965); C. Epstein et al., Eur J Biochem 82: 453–461 (1978); and P. Datta (1970), supra) but there are no reports in the literature that this protein also contains AK activity.

SUMMARY OF THE INVENTION

The object of the present invention is provide an isolated and purified bifunctional protein from carrots with aspartokinase and homoserine activities which can be used to regulate the amino acid content of plants, in particular the lysine, homoserine, threonine, isoleucine and/or methionine content.

It is another object of the present invention to provide a DNA molecule with a DNA sequence coding for a homologous segment of the bifunctional carrot protein.

It is a further object of the present invention to provide a method of regulating the amino acid content in a plant by bringing an effective amount of the bifunctional protein in contact with the plant.

BRIEF DESCRIPTION OF THE DRAWINGS

FIG. 8,8A–8F. DNA sequence of carrot AK-HSDH and the deduced amino acid sequence. Also shown are the positions of the peptides whose amino acid sequence was determined.

FIG. 9,9A–9C. Comparison of carrot HSDH and E. coli AKI-HSDHI. The deduced amino acid sequence of the carrot HSDH was compared to the E. coli AKI-HSDHI using the GAP program of the University of Wisconsin Genetics Computer Group. Vertical lines indicate identical amino acids; dots indicate amino acids encoded by similar codons (double dot: codons differing in one nucleotide; single dots: codons differing in two nucleotides). An asterisk (*) under a pair of amino acids indicates identities shared by carrot AK-HSDH, the three E. coli proteins, B. subtilis AKII and yeast AK, a circle (o) indicates identities shared by the carrot protein, E. coli HSDHI and II, B. subtilis HSDH and D. glutamicum HSDH.

DETAILED DESCRIPTION OF THE PREFERRED EMBODIMENTS

Figure 1:
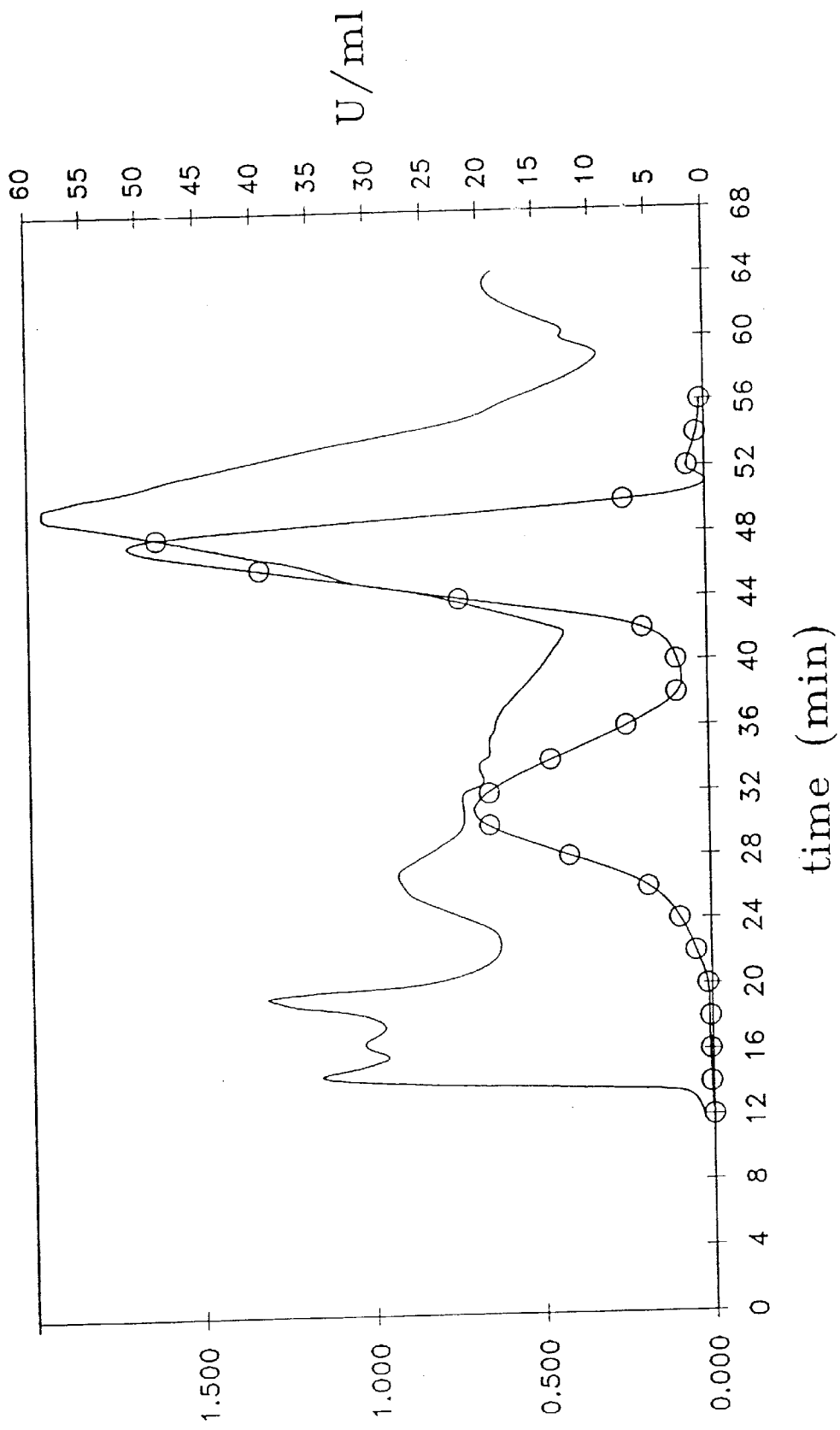
FIG. 1. Resolution of two peaks of AK activity. The AK activity (O) in U ml-1 of fractions eluted from the Altex Spherogel TSK-5PW DEAE (21.5 mm×15 cm) column equilibrated with 20 mM Mes pH 6, 5 mM 2-mercaptoethanol, 1 mM lysine, 1 mM threonine and 20% glycerol is shown. The protein profile detected by a Waters Lambda-max monitor set to 280 nm is expressed as relative absorbance units.
Figure 2A:
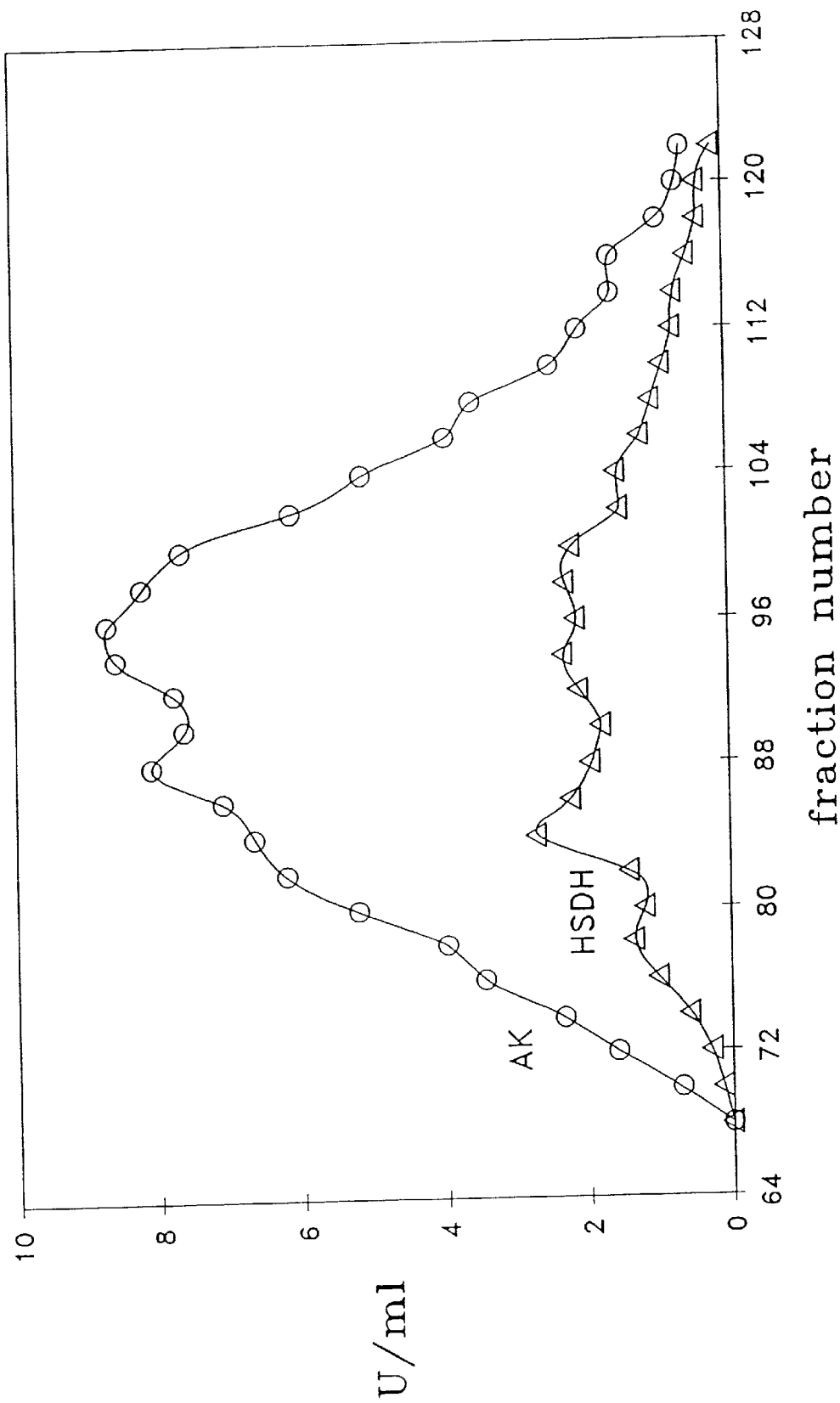
FIGS. 2A–E. Co-elution of AK and HSDH activities according to Table I. Fractions collected from gel filtration and anion exchange chromatography were assayed for AK and HSDH activities.
Figure 2B:
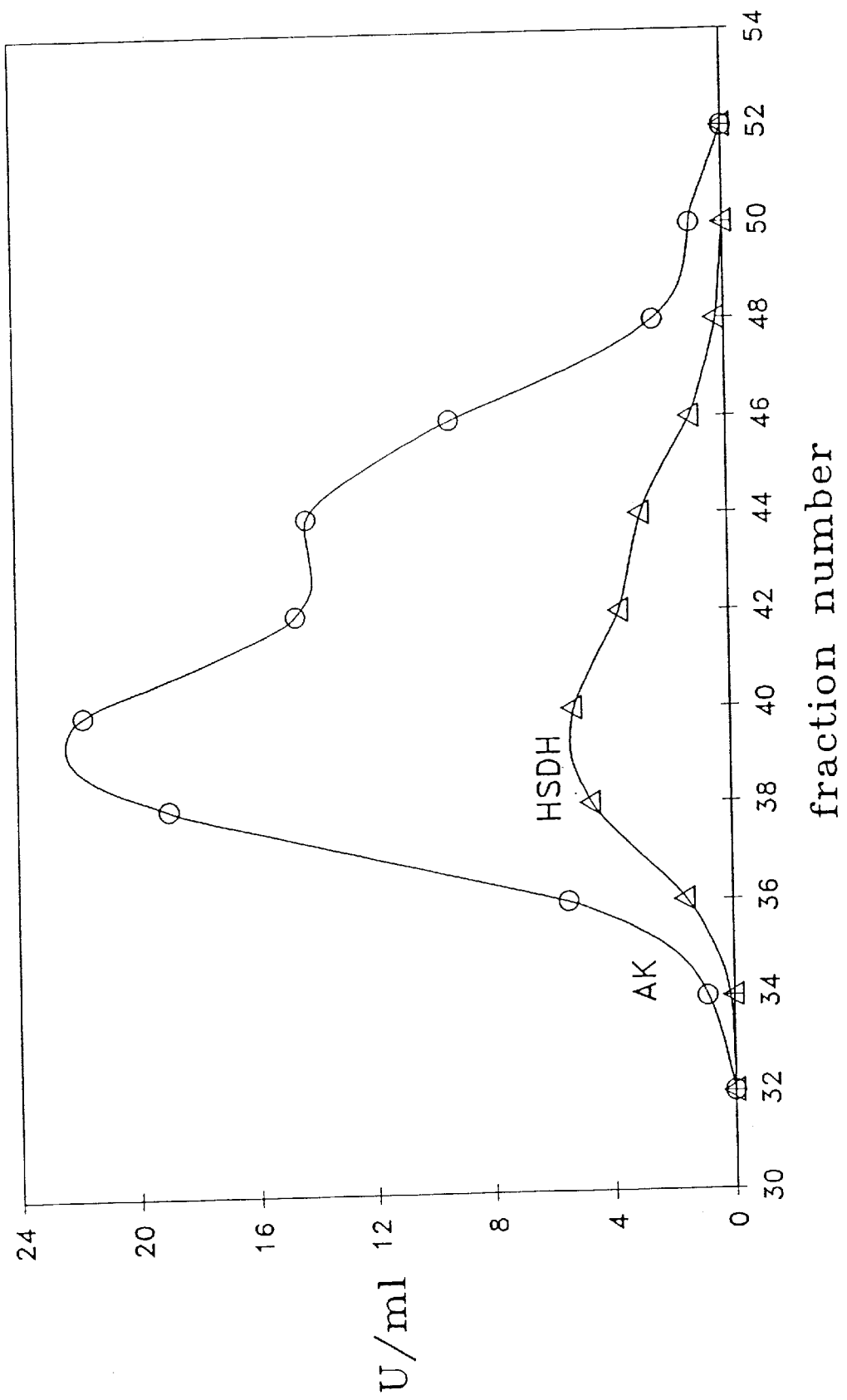
Figure 2C:
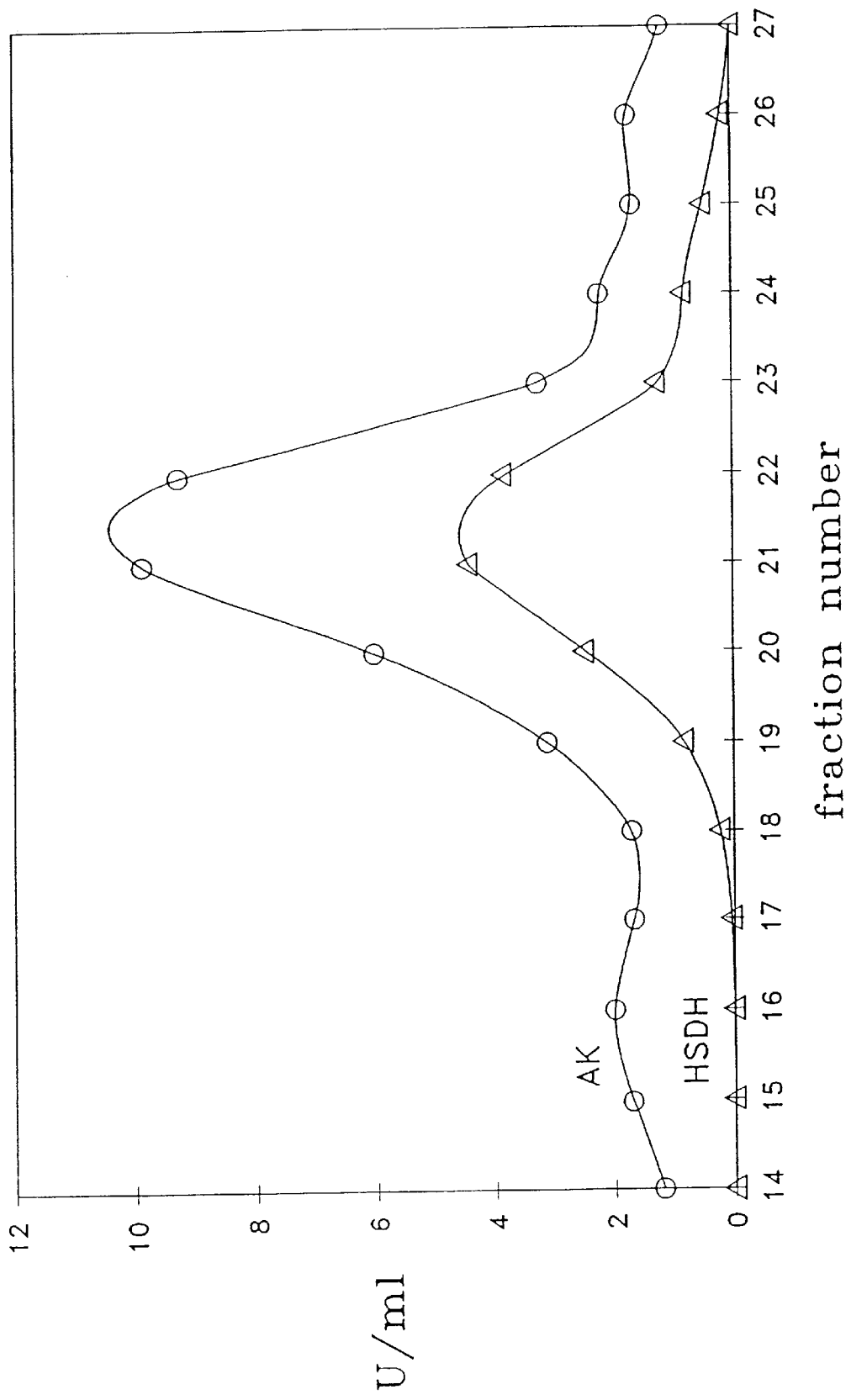
Figure 2D:
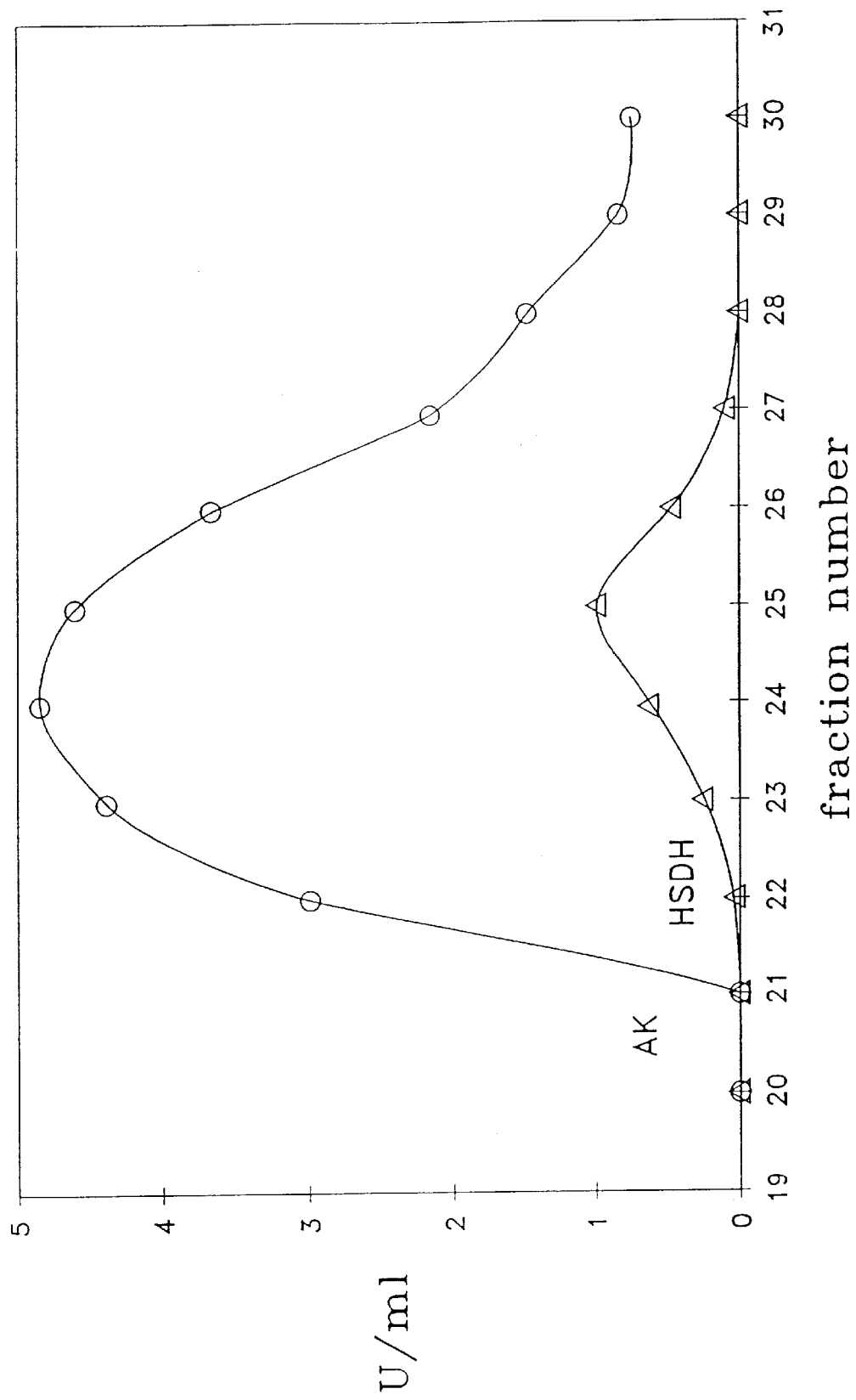
Figure 2E:
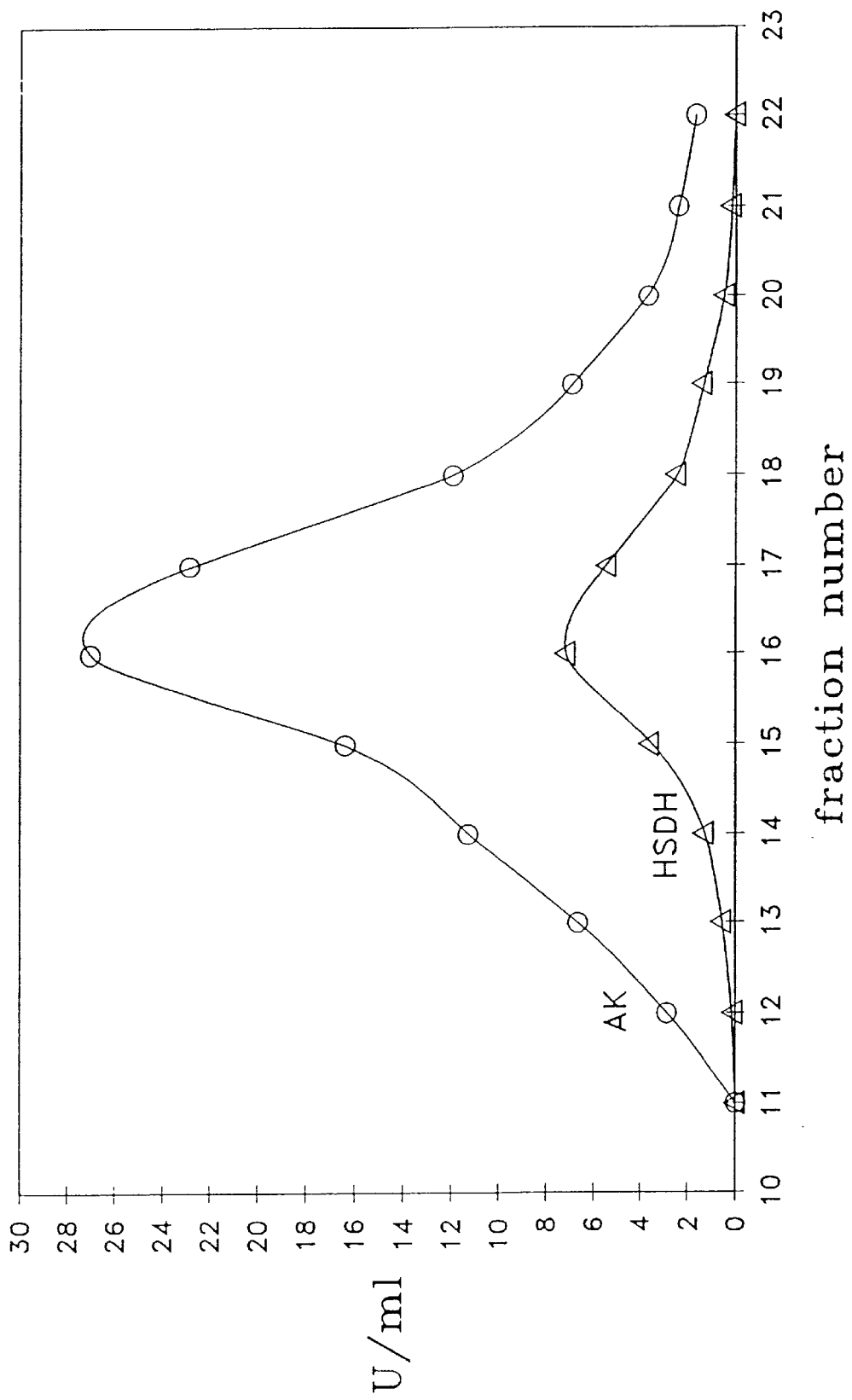

A native carrot protein has been identified to contain both aspartokinase and homoserine dehydrogenase activities and has been purified, isolated and characterized. A recombinant DNA molecule of the bifunctional enzyme has been constructed from mRNA of carrot cell suspension sultures. The activities of the enzyme are important in the biosynthesis of the nutritionally important essential amino acids lysine, threonine, methionine and isoleucine. Further, the gene and enzyme activities also may be important in synthesis of the precursor molecules of the plant hormone, ethylene.

In particular, the purified enzyme and recombinant DNA construct will be useful (1) in analyzing plant tissue to determine if they have this sequence or a similar sequence; (2) in determining the expression of the gene in the plant and specific plant tissue; (3) in making new constructs having one or the other enzyme activity; (4) in altering the recombinant DNA sequence to alter the regulation of these enzyme activities, especially to alter the amounts of the amino acid aspartate, and the nutrionally essential amino acids lysine, threonine and methionine, thus altering the nutrional value of plants, and the hormone, ethylene; (5) in identifying related sequences which also encode aspartokinase, homoserine dehydrogenase, or both; (6) in identifying their enzymes and how they are expressed; (7) in identifying DNA regulatory regions controlling the expression of this and related genes; (8) in synthesizing bulk quantities of this bifunctional plant enzyme; and (9) in gene transfer experiments as a marker.

Additionally, a DNA construct of the bifunctional enzyme gene will be useful in the field of molecular biology, particularly in the agricultural sciences. Seeds from certain crop plants are nutritionally deficient in essentail amino acids. For example, barley is low in available lysine, while soybean is low in methionine. It may be possible to improve the nutritional value of some crop plants by examining and altering the genes involved in amino acid biosynthesis, thus increasing the desired amino acid.

Homoserine dehydrogenase was purified to homogeneity and polypeptide fragments derived from digests of the protein were subjected to amino acid sequencing. Unexpectedly, the amino acid sequence of homoserine dehydrogenase from carrot indicates that both aspartokinase (AK) and homoserine dehydrogenase (HSDH) activities reside on the same protein. Additional evidence that aspartokinase and homoserine dehydrogenase reside on a bifunctional protein was provided by coelution of activities during purification steps and by enzyme specific gel staining techniques.

Highly purified fractions containing aspartokinase activity were stained for aspartokinase activity, homoserine dehydrogenase activity and protein. These gels supported the conclusion that aspartokinase activity and homoserine dehydrogenase activity were present on the same protein.

The comparison of the amino acid sequences of carrot with the other known sequences suggests that the carrot AK-HSDH is most closely related to the AKI-HSDHI of E coli because of the greater sequence homology at the AK portions of the protein. The carrot acid sequence has higher identify with the AKI-HSDHI than AKI-HSDHI has with the other E. coli fused protein AKII-HSDHII. Both carrot AK-HSDH and E. coli AKI-HSDHI are bifunctional enzymes with HSDH activities sensitive to threonine concentrations. The molecular weight of the subunit from carrot (85 kD) similar to the subunits of E. coli AKI-HSDHI (86 kD) and AKII-HSDHII (88 kD). The sequence obtained from carrot is more like the sequences from the E. coli bifunctional sequences than the other known prokaryotic HSDHs. Although different AK activities have been observed in carrot, it is not clear if these are separate gene products as in E. coli. Besides the differences in inhibition to end products, the $K_{m(asp)}$ are also different. However unlike E. coli, these different AKs in carrot may have a kinetically similar HSDH. Ligand binding is known to affect activity of the E. coli AKI-HSDHI. It has already been demonstrated that K+ or threonine binding alters the carrot HSDH. The regulation by ligand binding of a protein with two enzymatic activities can be very complex.

Protein with AK activity was partially purified by gel filtration and anion exchange chromatography. The total protein and enzymatic activity at each purification step are listed in Table I. Two peaks of AK activity were eluted from the DEAE column at pH 6.0 and identified according to their position of elution. FIG. 1 shows the resolution of two peaks of AK activity. The AK activity (O) in U ml-1 of fractions eluted from the Altex Spherogel TSK-5PW DEAE (21.5 mm×15 cm) column equilibrated with 20 mM Mes pH 6, 5mM 2-mercaptoethanol, 1 mM lysine, 1 mM threonine and 20% glycerol as shown. The protein profile detected by a Waters Lambda-max monitor set to 280 nm is expressed as relative absorbance units. DEAE is a beaded cellulose matrix crosslinked with epichlorohydrin producing diethylaminoethyl functional groups. Sephadex is a modified dextran matrix. Altex Sepherogel TSK-5PW DEAE has a base material of hydrophilic polymer derived from the Sepherogel TK 5000PW resin with the functional group DEAE (see above).

The first eluting peak (28–32 min), AKI, was inhibited by lysine and was relatively insensitive to threonine (See Table II). The second peak (44–48 min), AKII, was inhibited by threonine and was relatively insensitive to lysine. These two peaks were kinetically different as well as having different feedback inhibition patterns. The $K_{m(asp)}$ for AKI was approximately 1 mM and for AKII was approximately 9 mM. Experimental conditions could affect which AK activities were observed. AK activity inhibited by lysine was not observed unless lysine was added to the homogenization buffer. If the pH of the sample was lowered to pH 6 before anion exchange, sensitivity to lysine was lost, although the total amount of AK activity remained unchanged. If AK activity with sensitivity to both lysine and threonine were applied to cation exchange medium, activity did not bind even at pH 5 and sensitivity to lysine was lost. The amount of activity recovered in the wash was comparable to that applied. Furthermore, the lysine-sensitive activity could not be eluted from the cation-exchange medium with KCl.

TABLE I

Purification of Aspartokinase

| Sample[a] | Enzyme Units | Protein mg | Specific Activity[b] | Fold Purification | % |
|---|---|---|---|---|---|
| Recovery | | | | | |
| Crude | 1590 | 2870 | 0.55 | — | — |
| Biogel A-0.5 | 1550 | 590 | 2.6 | 4.8 | 97 |
| Sephadex G-150 | 1130 | 190 | 5.8 | 11 | 71 |
| DEAE, ph 6.0 | | | | | |
| Peak I | 180 | 10 | 17 | 30 | 11 |
| Peak II | 58 | 4.3 | 14 | 24 | 3.6 |
| DEAE1 pH 7.5 | | | | | |
| Peak I | 81 | 4 | 20 | 36 | 5.1 |
| Peak II | 45 | 3 | 15 | 15 | 2.8 |
| DEAE, pH 7.5, aspartate | | | | | |
| Peak I | 4 | 0.13 | 31 | 56 | 0.25 |
| Peak II | 4 | 0.25 | 16 | 30 | 0.25 |

[a]Data from 10 preparations were averaged.
[b]Expresses as units g-1 protein.

Both forms of AK has HSDH activity associated with them, although the ratio of AK:HSDH activity was not constant (See Table II). This ratio did not correlate with the inhibition pattern of the AK form of the enzyme. Even though the AK forms were different, all had HSDH activity that was sensitive to threonine. The HSDH and AK activities co-eluted during all steps of the purification procedure. FIG. 2 shows the co-elution of AK and HSDH activities according to Table I. Fractions collected from gel filtration and anion exchange chromatography were assayed for AK and HSDH activities.

No HSDH activity was detected for AK I after the anion exchange step at pH 6 but this activity could be measured after anion exchange at pH 7.5. In contrast to AKI, HSDH activity was detected with AK II after chromatography at pH 6.

Lane 5. ak31 with 0.09 U of AK (mix of Forms I and II) and 5.4 U of HSDH.

Figure 3:
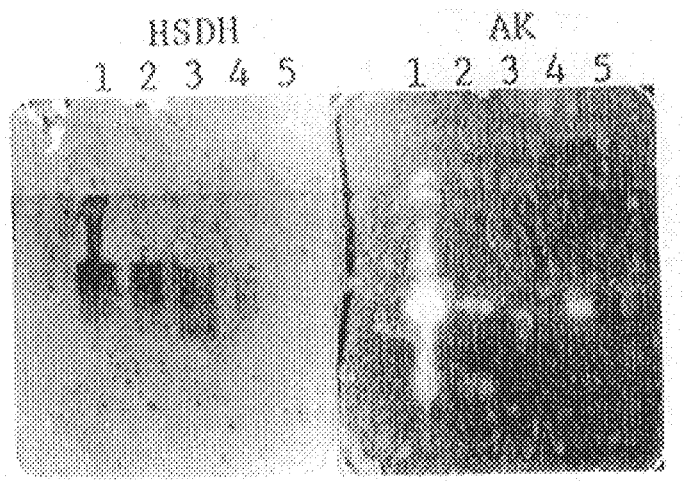
FIG. 3. AK and HSDH activity stains on polyacrylamide gels. Samples (4 ul) of forms I and II were loaded onto 8–25% polyacrylamide gel. The gel was first stained for AK activity and photographed and then stained for HSDH activity and photographed. Lane 1: ak44 with 1.2 U of AK (Form II) and 127 U of HSDH; Lane 2: ak44with 0.08 U of AK (mix of Forms I and II) and 7 U of HSDH; Lane 3: akxx (mixture) with 0.1 U of AK (Form II) and 7 U of HSDH; Lane 4: ak32 with 0.09 U of AK (Form I) and 1 of HSDH; Lane 5. ak31 with 0.09 U of AK (mix of Forms I and II) and 5.4 U of HSDH.

With Form II there was usually only one band of AK activity but the HSDH activity appeared as a ladder extending above the AK band (FIG. 3). This ladder has been described as aggregates of HSDH (Matthews (1989), supra). Lack of AK activity appearing with the HSDH activity ladder was thought to be due to the lack of sensitivity of the AK activity stain on gels. A very active sample of AK (AK44II) which has about ten times the activity of most AK samples gives a ladder of AK as well as HSDH activity on a gel (FIG. 3).

The cross reactivity with forms of AK by antibody made to purified carrot HSDH (Turano, supra) was investigated. Equal amounts of protein of each AK form were subjected to PAGE. Half of the gel was stained for HSDH activity and

TABLE II

Inhibition pattern of AK and Ratio of Dual Activities

| | U ml-1 | | Ratio | % Control AK activity | |
|---|---|---|---|---|---|
| Prep Number | AK | HSDH | AK/HSDH | +lys (10 mM) | +thr (10 mM) |
| ak321 | 22 | 360 | 0.06 | 21 | 68 |
| ak331 | 8 | 2200 | 0.004 | 39 | 71 |
| ak3311 | 8 | 5600 | 0.002 | 75 | 32 |
| ak4511 | 48 | 3200 | 0.02 | 91 | 33 |

In addition to the co-purification of AK and HSDH activities, the activities co-migrated on native PAGE. All three forms of AK had a bank of AK activity migrating to the same location on native PAGE. Frequently, forms I and III had an additional faster-migrating band of AK activity appearing on gels but HSDH activity appeared consistently with the slower-migrating band.

FIG. 3 shows the AK and HSDH activity stains on polyacrylamide gels. Samples (4 ul) of forms I and II were loaded onto 8–25% polyacrylamide gel. The gel was first stained for AK activity and photographed and then stained for HSDH activity and photographed. Lane 1: ak44 with 1.2 U of AK (Form II) and 127 U of HSDH; Lane 2: ak41 with 0.08 U of AK (mix of Forms I and II) and 7 U of HSDH; Lane 3: akxx with 0.1 U of AK (Form II) and 7 U of HSDH; Lane 4: ak32 with 0.09 U of AK (Form I) and 1 of HSDH;

the other half was electroblotted onto nitrocellulose. Form I had about half the HSDH activity of form II and the sample that was a mixture of forms I and II; all had different AK activity. The nitrocellulose blot was incubated with antibody specific to carrot HSDH (Turano, supra). Antibody bound to all three samples of AK (FIG. 4) indicating immunological similarity amongst the forms.

Figure 4:
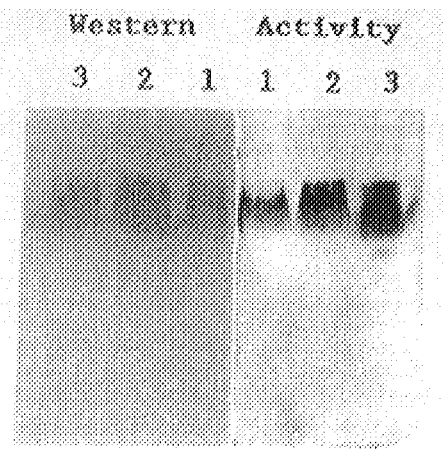
FIG. 4. Western blot of samples of AK with antibody against HSDH. Equal amounts of protein (4 ug) of samples of AK I, II and III were loaded onto 10–15% polyacrylamide gels. Half of the gel is electroblotted onto nitrocellulose for incubation with antibody and half is stained for HSDH activity. Lane 1: ak6 (Form I) with 6 U HSDH; Land 2: ak33 (Form II) with 22 U HSDH; Lane 3: ak20 (mix of Forms I and II) with 15 U HSDH.

FIG. 4 shows the Western blot of samples of AK with antibody against HSDH. Equal amounts of protein (4 ug) of samples of AK I, II and III were loaded onto 10–15% polyacrylamide gels. Half of the gel is electroblotted onto nitrocellulose for incubation with antibody and half is stained for HSDH activity. Lane 1: ak6 (Form I) with 6 U HSDH; Land 2: ak33 (Form II) with 22 U HSDH; Lane 3: ak20 (mix of Forms I and II) with 15 U HSDH.

Further evidence that the two enzymatic activities reside on the same polypeptide is provided by amino acid sequence data. Two peptide fragments derived from purified HSDH were sequenced. A sequence of 29 amino acids were obtained from peptide 97 (See Table III). This sequence had some identity with portions of known HSDH genes from prokaryotes (Matthews (1989), supra), especially with the HSDH regions of the two *E. coli* HSDHs (Table III). Carrot HSDH possessed 48% identity with the corresponding section of both AKI-HSDHI (ThrA) and 52% identity with AKII-HSDHII (MetL). The carrot HSDH possessed only 38% amino acid identity with HSDH from *Bacillus subtilis* and 34% identity with *Brevibacterium lactofermentum*.

*E. coli* bifunctional AKI-HSDHI than to *E. coli* AKII-HSDHII or to the *B. subtilis* AK and HSDH which are separate proteins. The identity of the carrot AK-HSDH with *E. coli* AKI-HSDHI was greater than the identity between any other two sequences; for example, the identity between *E. coli* AKI-HSDHI and *E. coli* AKII-HSDHII was only 34% for peptide. The locations of the sequenced peptides from carrot have been identified on the AKI-HSDHI and are shown in FIG. 5.

Figure 5:
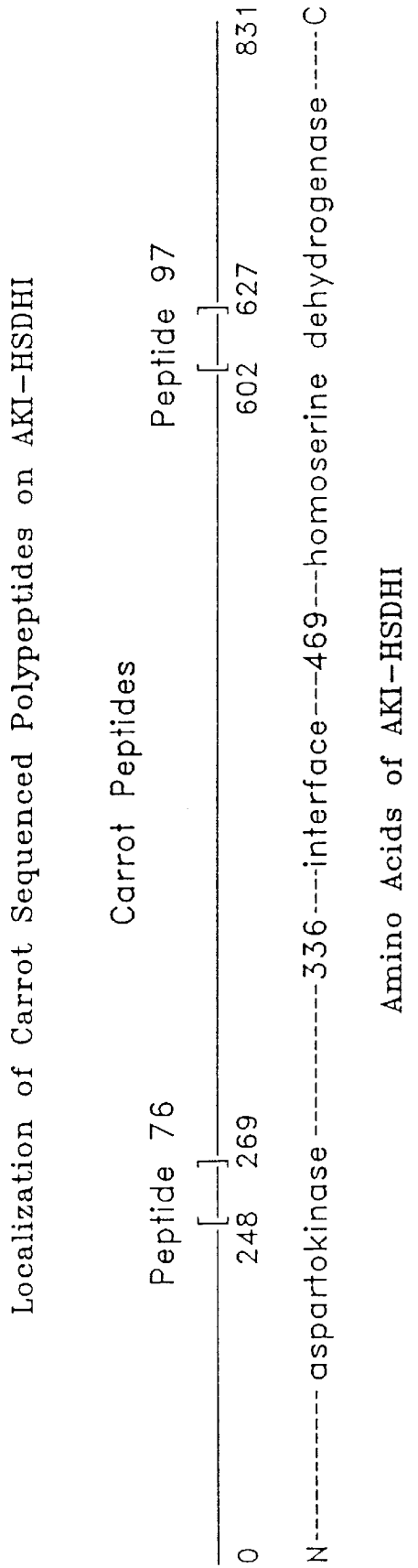
FIG. 5. Localization of carrot sequenced polypeptides on E. coli AKI-HSDHI. The peptide sequences from FIGS. 3 and 4 are indicated on the homologous region of E. coli AKI-HSDHI. The regions of the E. coli protein with AK and HSDH activities are shown on either side of an interface region.

In FIG. 5, localization of carrot sequenced polypeptides on *E. coli* AKI-HSDHI is shown. The peptide sequences from FIGS. 3 and 4 are indicated on the homologous region of *E. coli* AKI-HSDHI. The regions of the *E. coli* protein

TABLE III

Sequence Identity of Peptide 97

| Source | Amino Acid Sequence | % Identity | Ref |
|---|---|---|---|
| carrot | SerTyrThrHisTyr PheTyr—GluAlaThr ValGlyAlaGlyLeu ProIleIleThrThr LeuGlnGlyLeuLeu GluThrGlyAsp (SEQ ID NO:1) | | |
| thrA (AKI-HSDHI) | SerArgArgLysPhe LeuLys—AspIleAsn ValGlyAlaGlyLeu ProValIleGluAsn LeuGlnAsnLeuLeu AsnAlaGlyAsp (SEQ ID NO: 2) | 48 | 11 |
| metL (AKII-HSDHII) | ThrGlyArgHisTrp LeuTyr—AspIleAsn ValGlyAlaGlyLeu ProIleAsnHisThr ValArgAspLeuIle AspSerGlyAsp (SEQ ID NO: 3) | 52 | 24 |
| Bacilis subtilis | GluAsnGlycysAsp ThrTyrPheGluAlaSer ValAlaGlyGlyIle ProIleLeuArgThr LeuGluGluGlyLeu SerSer-Asp (SEQ ID NO: 4) | 38 | 4 |
| Bacilis lactofermentum | —Asn—ValAsp LeuTyrpheAlaAla ValAlaGlyAlaLeu ProValValGlyPro LeuArgArgserLeu —AlaGlyAsp (SEQ ID NO: 5) | 34 | 12 |

A sequence of 21 amino acids was obtained from peptide 76. This sequence corresponded to a portion of the amino acid sequence of several known aspartokinases (See Table IV) from prokaryotes and yeast (M. Cassan et al., *J Biol Chem* 261: 1052–1057 (1986); M. Katinka et al., *Proc Natl Acad Sci, USA* 77: 5730–5733 (1980); M. Zakin et al., *J Biol Chem* 258: 3029–3031 (1983); N. Chen, supra, J. Rafalski, supra). The amino acid identity between the carrot AK and the corresponding AK region of AKI-HSDHI (ThrA) of *E. coli* was 76% and identity was both AKIII(LysC) of *E. coli* and AK from *B. subtilis* was 52%. The identity with AKII-HSDHH (MetL) was 43% and was only 38% with yeast AK.

with AK and HSDH activities are shown on either side of an interface region.

Oligonucleotides based on amino acid sequences from the purified protein were used to amplify a DNA fragment from carrot cell culture RNA. The amplification product was used to probe cDNA libraries from carrot cell culture and root RNA. Two overlapping clones were isolated. Together the complete cDNA clone is 2915bp long and has a single long open reading frame for 864 amino acids. The isolated carrot cDNA encodes a bifunctional aspartokinase-homoserine dehydrogenase enzyme.

Previous studies of plant enzymes gave no evidence of the existence of a bifunctional AK-HSDH in plants. Such forms

TABLE IV

Sequence Identity of Peptide 76

| Source | Amino Acid Sequence | % Identity | Ref |
|---|---|---|---|
| carrot | ThrLeuAspTyrGln GluAlaTrpGluMet SerTyrPheGlyAla AsnValLeuHisPro Arg (SEQ ID NO: 6) | | |
| thrA (AKI-HSDHI) | SerMetSerTyrGln GluAlaMetGluLeu SerTyrPheGlyAla LysValLeuHisPro Arg (SEQ ID NO: 7) | 76 | 11 |
| metL (AKII-HSDHII) | LeuLeuArgLeuAsp GluAlaSerGluLeu AlaArgLeuAlaAla ProValLeuHisAla Arg (SEQ ID NO: 8) | 43 | 24 |
| LysC (AKIII) | GluIleAlaPheAla GluAlaAlaPheMet AlaThrPheGlyAla LysvalLeuHisPro Ala (SEQ ID NO: 9) | 52 | 3 |
| Bacilis subtilis | GlylleserTyrAsp GluMetLeuGluLeu AsnLeuGlyAla GlyvalLeuHisPro Arg (SEQ ID NO: 10) | 52 | 4 |
| yeast | SerValThrProGlu GluAlaSerGluLeu ThrTyrTyrGlySer GluValIleHisPro Arg (SEQ ID NO: 11) | 38 | 18 |

When the amino acid identities of the two sequences from carrot were compared to other known AK and HSDH sequences, carrot was found to be more closely related to the had not been found outside of the Enterobacteriaceae. The DNA sequence of the isolated carrot cDNA, as well as further analysis of the carrot enzyme, unexpectedly reveal that carrot has a bifunctional AK-HSDH similar to that found in *E. coli*. The most common situation is the existence of separate aspartokinase and homoserine dehydrogenase proteins. Since the carrot cDNA is the first aspartokinase or homoserine dehydrogease clone isolated from a plant, it is not known if such fused genes are common in plants. However, a partial clone isolated from soybean has approximately 80% identity to the carrot clone and appears to also encode both AK and HSDH.

Although the cDNA clone has a potential start site for translation, it is doubtful that this is the actual start. HSDH and AK have been shown to be localized in the chloroplasts of several plant species (J. Bryan et al., *Plant Physiol* 59: 673–679 (1977); P. Lea et al., *FEBS Lett* 98: 165–168 (1979); W. Mills et al., *Planta* 142: 153–160 (1978); J. Sainis et al., *Planta* 152: 491–496 (1981); and R. Wallsgrove et al., *Plant Physiol* 71: 780–784 (1983)) and are probably localized in the chloroplast of carrot. It follows that the carrot AK-HSDH probably has a chloroplast transit peptide at the amino terminus, since all known proteins transported into the chloroplast have transit peptides (K. Keegstra et al., *Annu Rev of Plant Physiol and Plant Mol Biol* 40: 471–501 (1989)). The reading frame of the clone is continuous from the second base pair through the conserved KFGGT sequence which is found near the amino-terminus of all AK proteins. The 30–35 amino acids encoded by the 5' end of the clone have the character of chloroplast transit peptides: the string is rich in serine, threonine, and small hydrophobic amino acids (K. Keegstra, supra). The sequence of the amino-terminus of the purified HSDH could not be determined and no precursor with a transit peptide has been identified.

Availability of the AK-HSDH bifunctional enzymes in mass quantity provides the opportunity to introduce regulation and control of plant conversion of aspartate to the amino acids methioninem threonine, lysine and isoleucine. Either by directly applying the enzyme to plants or by inserting the controlling genes into seeds, one can alter the amino acid concentration in food sources. Since availability of quantities of the enzymes is a major limiting factor in the commercial use of the isolated and purified enzymes; reliable sources must be secured prior to field trials and large scale test implementation. Using conventional biotechnology techniques, such sources can be secured.

Using conventional techniques such as dideoxy chain termination method of Sanger et al., supra, the DNA sequence can be determined for the proteins which encode the amino acid sequence of the homologous segement of the purified and isolated bifunctional enzyme. The phrase "homologous segment of the enzyme" means an amino acid sequence sufficiently duplicative of the protein of the present invention to allow the possession of the unique properties of the isolated and purified bifunctional enzyme.

Two DNA sequences are "substantially homologous" when at least 77 to 90%, preferably 80 to 90% and most preferably 85%, of the nucleotides match over the defined length of the selected region that encodes for the enzyme. Defining appropriate hybridization conditions is within the skill of the art.

On the basis of the genetic code, there exits a finite set of nucleotide sequences which can genetically code for a given amino acid sequence. All such equivalent nucleotide sequences are operable variants of the disclosed sequence, since all give rise to the same protein, having the same amino acid sequence, during the course of an in vivo transcription and translation. Consequently, all such variants are intended to be included in the scope of the present invention.

A cDNA expression library was constructed in the bacteriophage vector lambda-gt11 using poly A mRNA purified from carrot cell culture and carrot root. The cDNA library was screened with using radiolabelled PCR product as a probe. The coding sequence can be contained in vectors which are operable as cloning vectors or expression vectors when inserted into an appropriate host. The expression vector may be for example a replicon, plasmid, bacteriophage, virus or hybrid thereof. The vectors used in practicing the invention are selected to be operable as cloning vectors or expression vectors in the selected host cell. Numerous cloning vectors known to those skilled in the art, and selection of an appropriate cloning vector is a matter of choice. Examples of cloning vectors include the bacteriophage lambda-gt11, M13mp18 amd mp19. See generally Maniatis et al., DNA Cloning: A Practical Approach, Volumes I and II (D. Glover, ed.) IRL Press, Oxford (1985); and J. Sambrook et al., Molecular Cloning: A Laboratory Manual, 2nd Edition, Cold Spring Harbor Press, Cold Spring Harbor, N.Y. (1989).

The encoding DNA or expression vector of the present invention can be expressed in mammalian cells or other eukaryotic cells, such as yeast, or in prokaryotic cells, in particular bacteria. Bacterial strains may be utilized as hosts for the production of the enzymes of the present invention, such as *E. coli* strains and other enterobacteria such as *Salmonella, Serratia* and *Pseudomonas*.

The deduced amino acid sequence of the carrot HSDH shows homology to bacterial aspartokinases and homoserine dehydrognases and to yeast aspartokinase. The most striking homology is to the *E. coli* AKI-HSDHI protein. The overall homology between the carrot HSDH and *E. coli* AK-HSDH (48%) is higher than that between the two *E. coli* AK-HSDH proteins (39%) (M. Zakin, supra). It has been proposed that AKI-HSDHI consists of three domains: an amino-terminal domain with aspartokinase activity (amino acids 1 to approximately 249), a carboxy-terminal domain with homoserine dehydrogenase activity (amino acids 471 through 820), and an interface domain (amino acids 250–470) (J. Rafalski, supra). The regions of the carrot protein that are most similar to AKI-HSDHI are the interface and homoserine dehydrogenase domains. In contrast the homology between the carrot protein and *E. coli* AKII-HSDHII is lowest in the interface region. The homology in the other regions is only slightly lower for AKII-HSDHII than for AKI-HSDHI. Both the carrot enzyme and AKI-HSDHI are regulated by threonine, whereas AKII-HSDHII is not. The higher homology between the two proteins may be related to this regulation.

In order to understand the regulation of these genes and the enzyme activities one needs to know the number of genes and the number of distinct forms of the enzymes that exist. It has not been determined if the isolated cDNA represents the only AK or HSDH gene in carrot. Studies on the HSDH enzyme of carrot indicate that there is only one HSDH protein, but this protein has different subunit structure and different regulatory properties depending on solution conditions (Matthews ((1989), supra). Studies on the AK function have shown three forms of enzyme which differ in their sensitivity to lysine and threonine. Some of these forms appear to interconvert. There is no conclusive evidence yet as to whether all the forms of carrot AK and HSDH are separate proteins or if they are forms of the same protein. There is also no definitive proof that the cDNA clone described here represents the only carrot gene for AK and HSDH. DNA blots probed with the carrot cDNA indicated a low number of hybridizing sequences in the genome, and RNA blots showed predominantly one band of about 3000 nucleotides. However, genes with only slight variations may not have been seen as different in these experiments and genes with low homology might not be uncovered at all. In contrast to the carrot results, experiments with a soybean clone show a much more complex pattern of DNA and RNA hybridization4. It is possible that carrot has only the one AK-HSDH which has both enzymatic functions and is regulated both by threonine and lysine.

Having now generally described the invention, the same will be further understood by reference to certain specific examples which are included herein for purposes of illustration only and are not intended to be limiting.

EXAMPLE I
Plant Material and Enzyme Extraction

Cell suspension cultures of carrot (*Daucus carota* L. cv Danvers) were grown in flasks containing 200 ml of defined liquid medium as described in B. Mattews (1978), supra. HSDH activity was purified to homogeneity as described in B. Matthews (1989), supra. The proteins from polyacrylamide electrophoretic gels containing HSDH were blotted onto nitrocellulose paper and analysed for their amino acid sequencing. Sequence data was obtained from peptides separated by reverse-phase chromatography of digests of HSDH with trypsin, after it was determined that the N-terminal amino acid was blocked.

AK was purified by a series of column chromatography steps. The cells were harvested after 5 days and disrupted in a nitrogen bomb as described for HSDH (B. Matthews (1989), supra) except that the threonine concentration was reduced to 1 mM and 1 mM lysine was added to the extraction buffer. The crude extract was concentrated by 60% ammonium sulfate before the first gel filtration through Biogel A-0.5 m (4.5 cm×47 cm) equilibrated with 50 mM Tris-HCl pH 7.5, 10 mM 2-mercaptoethanol, 1 mM EDTA, 1 mM lysine, 1 mM threonine and 20% glycerol. Fractions containing AK activity were combined, concentrated by the addition of an equal volume of saturated ammonium sulfate for a second gel filtration through Sephadex G-150 (2.5 cm×39 cm) and equilibrated with the same buffer plus 0.2M KCl. Fractions with AK activity were combined, concentrated by the addition of an equal volume of saturated ammonium sulfate and dialyzed against 16 mM Tris-HCl pH 7.5, 10 mM 2-mercaptoethanol, 1 mM lysine, 1 mM threonine and 20% glycerol. The dialyzed sample was loaded onto an Altex Spherogel TSK DEAE-5PW column (21.5 mm×15 cm). AK activity was eluted over 65 min with a gradient from 0–0.5 M KCl in 20 mM Mes pH 6, 5 mM 2-mercaptoethanol, 1 mM lysine, lmM threonine, and 20% glycerol. Fractions containing activity were combined, diluted four-fold and applied to an Altex Spherogel TSK DEAE-5PW column (7.5 mm×7.5 cm) equilibrated with 50 mM Tris-HCl pH 7.5 containing 5 mM 2-mercaptoethanol, 1 mM lysine, 1 mM threonine and 20% glycerol fractions containing AK activity were combined and diluted four-fold and reapplied to the column equilibrated with the same buffer containing 20 mM aspartate. Fractions with AK activity were concentrated by filtration through Centricon-303 filters (Amicon) and stored at −20° C.

EXAMPLE II
Enzyme and protein assays and stains

Aspartokinase activity was assayed by the hydroxamate method as described in P. Bryan et al., *Biochem Biophys Res Comm* 41: 1211–1217 (1970). The assay mixtures contained 100 mM Tris, pH 8.0, 50 mM hydroxamate-KOH, 50 mM L-aspartate, 40 mM ATP, and 20 mM Mg2SO4 and were incubated at 37° C. for 60 min. The reaction was terminated by the addition of a solution of 0.37M FeCl3, 0.20M trichloroacetic aid and 0.72M HCl. One unit (U) of activity produced 1 mmol β-aspartylphosphate hr$^{-1}$. Zero time controls were included. Activity was visualized on polyacrylamide gels (Phast System by Pharmacia, Upsala, Sweden) by incubating gel slices at 37° C. in 50 mM Tris-HCl pH 7.5, 50 mM aspartate 10 mM ATP, 50 mM MgSO4, 1 mM DTT, 20% glycerol, 0.014 gm ml$^{-1}$10.02% Alizarin red S (H. Nimmo et al., *Anal Biochem* 121: 17–22 (1982); and J. Relton, supra). To show specific aspartate kinase activity, duplicate gel strips were incubated without aspartate and also in aspartate with 10 mM lysine and/or 10 mM threonine.

HSDH activity was assayed in the direction of coenzyme reduction as described in B. Matthews (1989), supra. Enzyme preparations were analyzed on 8–15% gradient polyacrylamide gels using a Phast (Pharmacia, Upsala, Sweden) gel electrophoresis system. HSDH activity was located on the gel as described in B. Mattews (1978), supra, using 60 mM Tris-HCl (pH 9.0), 150 mM KCl, 30 mM NAD+, 24 mM homoserine, 0.22 mM 2-mercaptoethanol, 0.15 mM EDTA, 0.266 mg ml$^{-1}$ nitro blue tetrazolium and 0.025 mg ml$^{-1}$ phenazine methosulfate incubated at 37° C. Gels incubated in the staining mixture lacking homoserine were used as controls.

Protein was visualized on gels using silver nitrate according to the manufacturer's instructions (Pharmacia).

EXAMPLE III
Western Blot Analysis

The backing of the Phast gel was removed using a razor blade. The protein in the polyacrylamide gel was then electroblotted onto nitrocellulose in 25 mM Tris, 20 mM glycine, pH 8.3 at 25–35 V for 1 hour at 4° C. Excess protein binding sites were blocked by incubating the filters in 1×TBS2, 1.0% dry milk and 0.5% BSA for a hour at room temperature. Nitrocellulose filters were incubated with primary antibody (anti-HSDH antiserum from mouse), secondary and tertiary antibody and the alkaline phosphatase activity visualized as described by F. Turano, supra.

EXAMPLE IV
General DNA Cloning Methods

Plasmid DNA preparation, ligations, restriction enzyme digestions, Southern blots, Northern blots were done according to standard procedures (T. Maniatis et al., *Molecular Cloning: A Laboratory Manual*, Cold Spring Harbor Laboratory, Cold Spring Harbor, N.Y. (1982)). Plant genomic DNA was extracted by the method of P. Keim et al., *Soybean Genetics Newsletter* 15: 150–152 (1988). Enzymes were obtained from either Bethesda Research Laboratories or Boehringer Mannehim. PCR reagents were from Perkin-Elmer Cetus. oligonucleotides used for PCR were obtained from Synthecell.

DNA probes were labelled with [β-$^{32}$P] dCTP (DuPont-New England Nuclear) using the random oligonucleotide priming method described by A. Feinberg, *Anal Biochem* 132: 6–13 (1983).

DNA sequence determination was done by the dideoxy chain termination method using modified T7 DNA polymerase (Sequenase 2.0 from United States Biochemical Corp.) (F. Sanger et al., *Proc. Natl. Acad. Sci. U.S.A.* 74: 5463–5467 (1977)).

EXAMPLE V
Construction of a Carrot cDNA Library

Total RNA was extracted from two-month old carrot roots using the method described by J. Chirgwin et al., *Biochem* 18: 5294–5299 (1979). Poly (A)+ RNA was isolated from total RNA on columns of oligo (dT) cellulose (Maniatis, supra). cDNA was made from 3 ug poly (A)+ RNA using the cDNA Synthesis System Plus from Amersham. EcoRI adaptors were added (Promega "Riboclone EcoRI Adaptor Ligation System") and the cDNA was ligated with lambda-gt11 arms (Promega) and packaged using Stratagene "Gigapack II Plus" packaging extracts. The phage were plated and screened following methods described by Maniatis, supra. Approximately 240,000 plaques were screened using a radiolabelled PCR product as the probe. Lifts were done in duplicate onto nitrocellulose filters. Filters were hybridized in 50% formamide/5× Denhardt's solution/5× SSPE/0.1% SDS/100 ug/ml denatured salmon sperm DNA at 42° C. for 18 hr. The final wash was with 0.1× SS/0.1% SDS at 45° C. for one set of filters and 60° C. for the second set.

A second CDNA library was constructed in the same manner, except that poly (A)+ RNA from carrot cell culture was used and first strand synthesis was primed with an oligonucleotide corresponding to a tryptic peptide from purified carrot HSDH (HSDH97: 5'-GCT/CTCA/GTAA/GAAA/GTAA/GTGNGTA/GTA). (SEQ ID NO: 12)

EXAMPLE VI
PCR Amplification of Carrot cDNA Encoding HSDH

HSDH protein purified from carrot cell suspension cultures was subjected to proteolysis and the polypeptides were separated by high pressure liquid chromatography (HPLC). The amino acid sequences of four polypeptides were determined. Based on the amino acid sequence of two of these polypeptides two oligonucleotides were synthesized:

Oligo HSDH 76: 5'-TAT/C CAA/G GAA/G GCN TGG GAA/G ATG (SEQ ID NO: 13) (Peptide 76: -NH$_2$-TyrGlnGluAlaGlnTrpGluMet (SEQ ID NO: 14)

Oligo HSDH 97: 5-GCT/CTC A/GTA A/GAA A/GTA A/GTG NGT A/GTA (SEQ ID NO: 15) (Peptide 97: AlaGluTyrPheTyrHisThrTyr-NH$_2$ (SEQ ID NO: 16)

These oligonucleotides were used as primers for PCR amplification of carrot cDNA. Both double-stranded cDNA made from carrot root poly(A)+ RNA and a first-strand cDNA made from carrot cell culture poly(A)+ RNA served as templates. When the amplification was carried out at an annealing temperature of 52° C., using either template, predominantly an 1100bp product was obtained.

Figure 6:
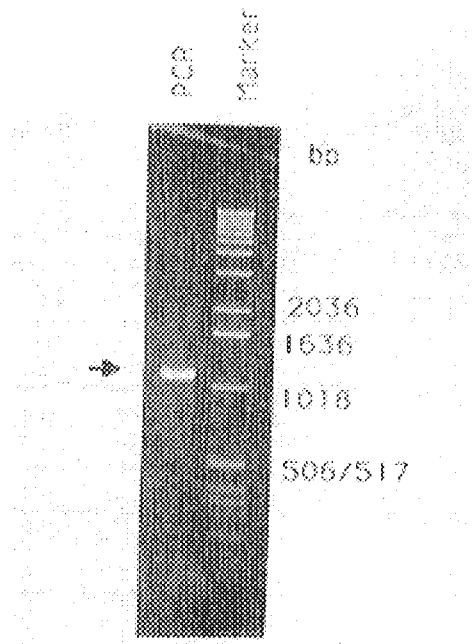
FIG. 6. Product of PCR amplification of a carrot cDNA segment encoding HSDH. Poly (A)+ RNA from carrot cell suspension cultures was used for first-strand cDNA synthesis. This cDNA was used as the template for PCR amplification with primers HSDH 76 and HSDH 9. Amplification was carried out at an annealing temperature of 52° C. for 30 cycles.

FIG. 6 shows the product of PCR amplification of a carrot cDNA segment encoding HSDH. Poly (A)+ RNA from carrot cell suspension cultures was used for first-strand CDNA synthesis. This cDNA was used as the template for PCR amplification with primers HSDH 76 and HSDH 9. Amplification was carried out at an annealing temperature of 52° C. for 30 cycles.

The PCR product was analyzed by restriction endonuclease digestion. A 579bp EcoRI-HindIII fragment was subcloned into vectors M13mp18 and mp19 and the DNA sequence was determined.

EXAMPLE VII
Isolation of Lambda-gt11 Carrot cDNA Clones for HSDH

The 1100bp PCR amplified DNA fragment was used to screen a carrot cDNA library. The library was constructed in the vector lambda-gt11 and contained cDNA from carrot root poly(A)+ RNA. From approximately 250,000 plaques four clones were obtained. All of the clones displayed similar restriction digestion patterns and appeared to differ from one another only in length.

The complete DNA sequence of the longest clone, HSDH1, was determined. The clone was 2079 bp long and had one long open reading frame starting at base 1 and reading through base 1755 for a total of 585 codons.

Figure 7:
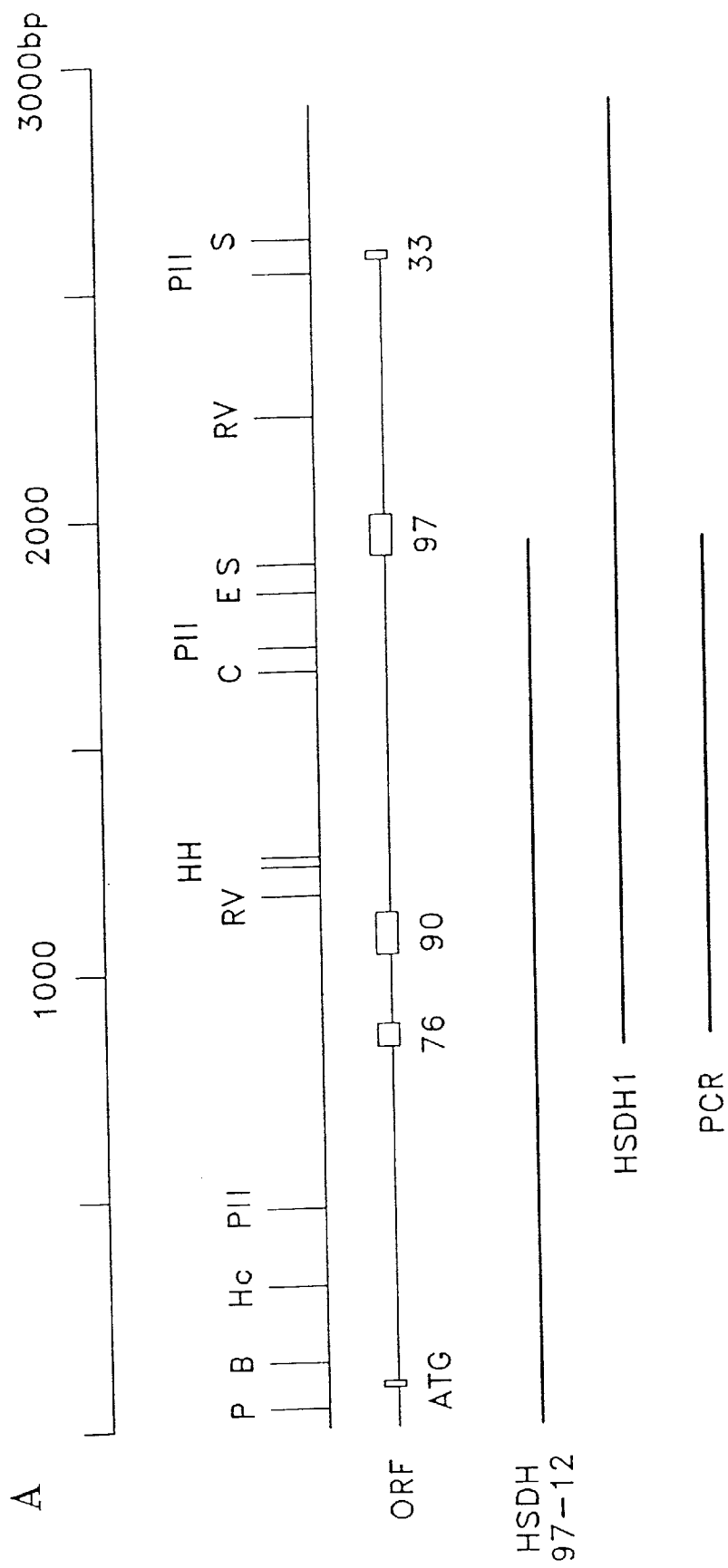
FIG. 7. Map of HSDH clones. Panel A: Restriction map of the full-length HSDH clone (P:PstI; B:BamHI; Hc:HincII; RV:EcoRV; H:HindIII; C:ClaI; E:EcoRI; S:SstI). Shown below this is the location of the 2591bp open reading frame, the potential start codon (ATG), and the positions of the sequenced peptides (76, 90, 97, 33).

FIG. 7 is a map of the HSDH clones. Panel A: Restriction map of the full-length HSDH clone (P:PstI; B:BamHI; Hc:HincII; RV:EcoRV; H:HindIII; C:ClaI; E:EcoRI; S:SstI). Shown below this is the location of the 2591 bp open reading frame, the potential start codon (ATG), and the positions of the sequenced peptides (76, 90, 97, 33).

Clone HSDH 1 had no apparent translation start site. RNA blot analysis using the HSDH PCR product as a probe identified a 3000 nucleotide transcript as the main hybridizing band. The open reading frame in the clone was not sufficient to code for a protein of 85,000+/−5000 daltons (the subunit size of the purified carrot enzyme (Matthews (1989), supra). These facts indicated that this clone was lacking approximately 1000 bp at the 5' end.

In order to enhance the probability of finding HSDH clones with a complete 5' end a second cDNA library using oligonucleotide HSDH97 to prime first-strand synthesis was constructed. The Poly (A)+ RNA was extracted from carrot cell culture. The cDNA was again cloned into a lambda-gt11 vector. 350,000 plaques were screened and fourteen positive clones were analyzed. Three of these contained inserts that extended beyond the 5' end of HSDH 1. The longest of these clones, HSDH 97-12, was 835 bp longer at the 5' end than HSDH1.

Figures 8, 8A, 8B, 8C, 8D, 8E, 8F:
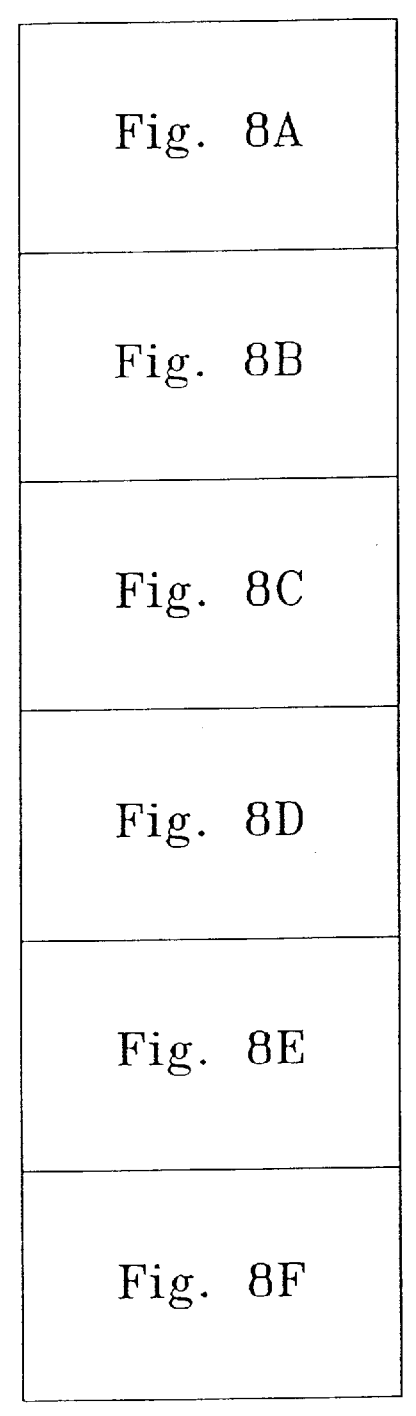

FIG. 8 shows the DNA sequence of carrot AK-HSDH and the deduced amino acid sequence. Also shown are the positions of the peptides whose amino acid sequence was determined.

EXAMPLE VIII
DNA Sequence Analysis and Comparison to Other Genes Coding for HSDH and AK The DNA sequence was determined for the total length of clones HSDH 1 and HSDH 97-12 and for parts of other clones. FIG. 8 shows the 2915 bp DNA sequence of the combined HSDH 1, HSDH 97-12 and other clones and the deduced amino acid sequence for the open reading frame from base pair 2 through base pair 2590. The sequences of four tryptic peptides from the purified carrot HSDH had been previously determined. These were compared to the deduced amino acid sequence from the cDNA clone and are also shown in FIG. 8. Only one amino acid residue out of 92 did not match ([S] in peptide 90) and this one was ambiguous in the peptide sequence.

The amino terminal sequence has not been determined for the carrot HSDH protein. There is a possible translation start site (ATG) at base pair 98 in the clone. If translation were to start at this site, the resulting 831 amino acid protein would have a molecular weight of 90,679 daltons, which is in the expected size range.

The deduced amino acid sequence of the carrot HSDH clone was compared to bacterial and fungal HSDH and AK proteins for which there is sequence information (See Table V). The strongest homology was between the carrot clone and the *E. coli* thrA gene.

Figures 9, 9A, 9B, 9C:
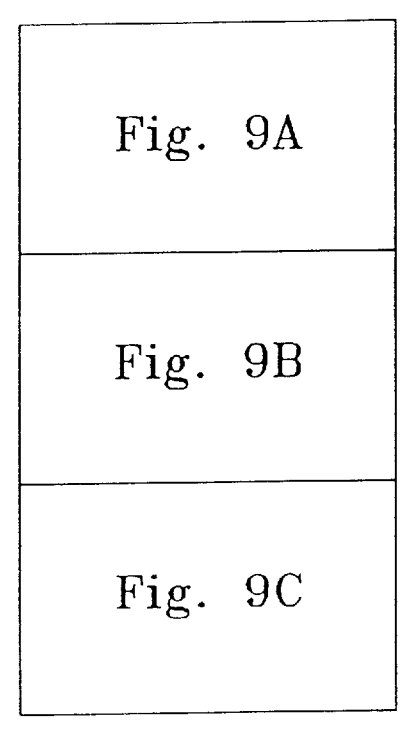

FIG. 9 shows a comparison of carrot HSDH and *E. coli* AKI-HSDHI. The deduced amino acid sequence of the carrot HSDH was compared to the *E. coli* AKI-HSDHI using the GAP program of the University of Wisconsin Genetics Computer Group. Vertical lines indicate identical amino acids; dots indicate amino acids encoded by similar codons (double dot: codons differing in one nucleotide;

single dots: codons differing in two nucleotides). An asterisk (*) under a pair of amino acids indicates identities shared by carrot AK-HSDH, the three *E. coli* proteins, *B. subtilis* AKII and yeast AK, a circle (o) indicates identities shared by the carrot protein, *E. coli* HSDHI and II, *B. subtilis* HSDH and *D. glutamicum* HSDH.

ThrA encodes the *E. coli* AKI-HSDHI bifunctional aspartokinase-homoserine dehydrogenase protein. *E. coli* AKI-HSDHI is 820 amino acids long; the amino-terminal 248 amino acids constitute the aspartokinase functional domain, the carboxy-terminal 324 residues constitute the homoserine dehydrogenase domain, and residues from abut 249 to 495 make up a central interface domain (Cohen (1987), supra). AKII-HSDHII has a similar structure. Proteins with only AK function (E. coli AKIII, *Bacillus subtilis* AKII, yeast AK) have homology to amino acids 1 through 500 of AKI-HSDHI. Proteins with only HSDH function (*Bacillus subtilis* HSDH, *Corynebacterium glutamicum* HSDH) have homology beginning at about amino acid 500 and extending through the carboxy-terminus of AKI-HSDHI. There is homology between the carrot HSDH and *E. coli* AKI-HSDHI along the full length of the proteins, although it is strongest in the HSDH domain and the interface domain. The homology with AKII-HSDHII is at a similar level, except in the interface region, where it is reduced.

TABLE V

Homology between carrot AK-HSDH and AK and HSDH proteins from other organisms.
Comparisons of the carrot AK-HSDH to the three enzymes from *E. coli*, to the AK of *Bacillus subtilis*, and to the HSDH from *Corynebacterium glutamicum* were made using the GAP program of the University of Wisconsin Genetics Computer Group. The comparisons to the *B. subtilis* HSDH and *Saccharoinyces cerevisiae* AK were based on published alignments between these proteins and the *E. coli* proteins (C. Parsot, et al., J. Biol Chem 263: 14654–60 (1988) and Rafalski, supra).

|  | % |  |  |
| --- | --- | --- | --- |
|  | Identity | Homologya | Total Identity + homology |
| *E. coli* AKI-HSDHI | 38 | 10 | 48 |
| Amino acid 33-282b | 30 | 9 | 39 |
| Amino acid 283-489 | 40 | 9 | 49 |
| Amino acid 490-864 | 40 | 10 | 50 |
| *E. coli* AKII-HSDHII | 33 | 9 | 42 |
| Amino acid 33-282 | 32 | 39 |  |
| Amino acid 283-489 | 19 | 9 | 28 |
| Amino acid 490-864 | 38 | 10 | 48 |
| *E. coli* AKIII | 28 | 12 | 40 |
| (Amino acid 33-500) |  |  |  |
| *B. subtilis* AKII | 33 | 9 | 42 |
| (Amino acid 33-502) |  |  |  |
| *B. subtilis* HSDH | 22 | 7 | 30 |
| (Amino acid 502-864) |  |  |  |
| *C. glutamicum* HSDH | 25 | 11 | 36 |
| (Amino acid 490-864) |  |  |  |
| *S. cerevisiae* A K |  |  |  |
| (Amino acid 33-405) |  |  |  | aAmino acid replacements: ile-val-leu, ser-thr, lys-arg, phe-tyr, glu-asp.
bAmino acid residue numbers refer to the amino acids of the carrot protein as shown in FIG. 9.

All aspartokinases analyzed have the sequence LysPheGlyGlyThr (SEQ ID NO:17) near the amino-terminus. This includes the yeast and *Bacillus subtilis* aspartokinases, *E. coli* AKIII, and *E. coli* AKI-HSDHI. *E. coli* AKII-HSDHII has the variation LysPheGlyGlySer (SEQ ID NO: 18). The deduced amino acid sequence of the carrot HSDH clone also has the LyspheGlyGlyThr (SEQ ID NO: 17) sequence (amino acids 38–42 in FIG. 9 and underlined in FIG. 8). Another highly conserved region contains the Gly-X-Gly-X-X-Gly motif which is presumed to be part of the NADH/NADPH binding domain of HSDH (C. Parsot, et al., *J Biol Chem* 263: 14654–60 (1988)). This is found in the carrot sequence at amino acids 512–517 as numbered in FIG. 9.

EXAMPLE IX
DNA and RNA Blot Analysis

All the carrot cDNA clones isolated appeared to represent the same gene. However, it was possible that there were additional genes for AK or HSDH. To test for the existence of other related mRNAs total carrot RNA was probed with the AK-HSDH clone.

Figure 10:
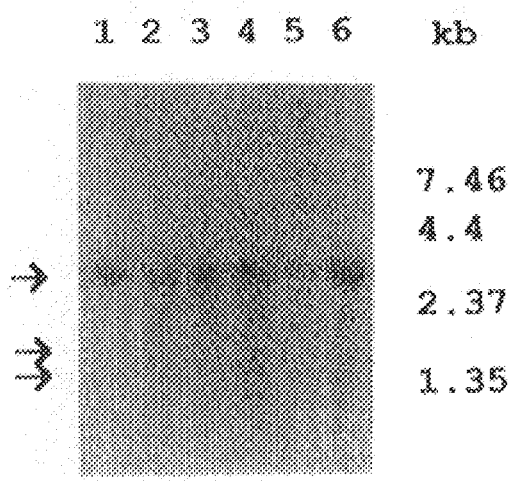
FIG. 10. Northern blot of carrot RNA probed with the HSDH clone. 10 ug of total RNA from each sample was run on an agarose-formaldehyde-formamide gel and transferred to nitrocellulose membrane. The blot was probed with a $^{32}$P-labelled 300 bp EcoRI-HincII fragment from the 5'-end of the clone. Hybridization was in 50% formamide/5× SSPE/5× Denhardt's/0.6% SDS/100 ug/ml denatured salmon sperm DNA at 42° C. for 18 hr. The final wash of the blot was in 0.1× SSC/0.1% SDS at 42° C. Lane 1–4: carrot cell culture (lane 1: 1 day; lane 2: 3 days; lane 3: 5 days, lane 4: 7 days and transfer); lane 5: 2 month old leaves; lane 6: 2 month old roots).

FIG. 10 shows a Northern blot of carrot RNA probed with the HSDH clone. 10 ug of total RNA from each sample was run on an agarose-formaldehyde-formamide gel and transferred to nitrocellulose membrane. The blot was probed with a $^{32}$P-labelled 300 bp EcoRI-HincII fragment from the 5'-end of the clone. Hybridization was in 50% formamide/5× SSPE/5× Denhardt's/0.6% SDS/100 ug/ml denatured salmon sperm DNA at 42° C. for 18 hr. The final wash of the blot was in 0.1× SSC/0.1% SDS at 42° C. Lane 1–4: carrot cell culture (lane 1: 1 day; lane 2: 3 days; lane 3: 5 days, lane 4: 7 days and transfer); lane 5: 2 month old leaves; lane 6: 2 month old roots).

The Northern blots showed predominantly a message of about 3000 nucleotides. Minor bands were also seen at about 1500 and 1250 nucleotides. It has not been determined if this is a breakdown product of the larger RNA or a second message. Although FIG. 10 shows a blot probed with a 300 bp fragment from the 5'-end of the clone, a similar pattern was seen when the full-length cDNA was used.

Figure 11:
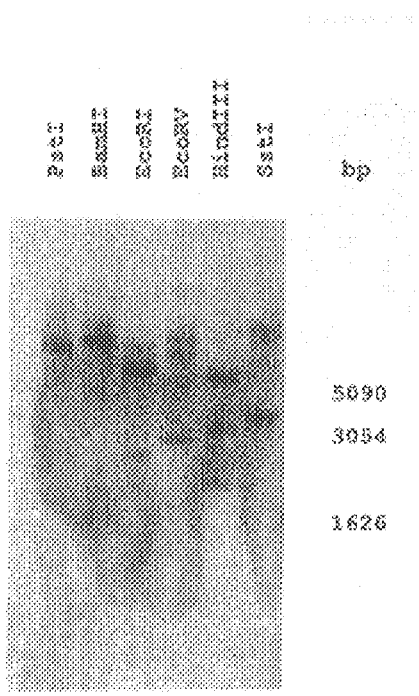
FIG. 11. Southern blot of carrot genomic DNA probed with the HSDH CDNA clone. Carrot leaf DNA was digested with the indicated restricted enzymes, run on an agarose gel and blotted to nitrocellulose membrane. The blot was probed with the full-length HSDH clone. Hybridization was in 25% formamide/5× SSPE/5× Denhardt's/0.5% SDS/100ug/ml denatured salmon sperm DNA at 42° C. for 23 hr. The final wash of the blot was in 2× SSC/0.2% SDS at 42° C.

Genomic carrot DNA was also probed with the AK-HSDH clone. FIG. 11 shows a Southern blot of carrot genomic DNA probed with the HSDH cDNA clone. Carrot leaf DNA was digested with the indicated restricted enzymes (restriction endonucleases), run on an agarose gel and blotted to nitrocellulose membrane. The blot was probed with the full-length HSDH clone. Hybridization was in 25% formamide/5× SSPE/5× Denhardt's/0.5% SDS/100 ug/ml denatured salmon sperm DNA at 42° C. for 23hr. The final wash of the blot was in 2× SSC/0.2% SDS at 42° C.

The blots were probed at low stringency and washed at both low and high temperatures. All the blots revealed fairly simple banding patterns, indicating a low number of hybridizing sequences in the genome. In contrast soybean genomic blots probed with the carrot HSDH clone showed a much more complex pattern. If there were related, but only partially homologous, sequences in the genome, higher wash temperatures should have removed the bands for these sequences preferentially from blots. This did not occur. Higher wash temperatures simply reduced the intensity of all bands.

The references cited above are all incorporated by reference herein, whether specifically incorporated or not.

Having now fully described this invention, it will be appreciated by those skilled in the art that the same can be performed within a wide range of equivalent paramenters, concentrations, and conditions without departing form the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims. It is to be understood that the phraseology or terminology employed herein is for the purpose of description and not of limitation.

What is claimed:

1. A purified and isolated bifunctional protein extracted from carrots wherein said protein is a means for regulating the lysine and homoserine content in plants and wherein said protein has both homoserine dehydrogenase and aspartokinase activity in the same polypeptide.

2. A protein according to claim 1 wherein said protein is a means for regulating the threonine, isoleucine or methionine content in plants.

3. A protein according to claim 1 comprising a peptide having an amino acid sequence having the formula Ser-TyrThrHisTyrPheTyrGlu AlaThrValGlyAlaGlyLeuProIleIleThrThrLeuGlnGlyLeuLeuGluThrGlyAsp (SEQ ID NO: 1).

4. A protein according to claim 1 comprising a peptide having an amino acid sequence having the formula Thr-LeuAspTyrGlnGluAlaTrp GluMetSerTyrPheGlyAlaAsn-ValLeuHisProArg (SEQ ID NO: 6).

5. A purified recombinant bifunctional protein produced by a host transformed or transfected with a polynucleotide molecule which is an expression vehicle, said polynucleotide molecule comprising a nucleotide sequence which encodes the protein according to claim 1.

* * * * *

SEQUENCE LISTING ( 1 ) GENERAL INFORMATION:

( i i i ) NUMBER OF SEQUENCES: 23

( 2 ) INFORMATION FOR SEQ ID NO:1:

( i ) SEQUENCE CHARACTERISTICS:
        ( A ) LENGTH: 29 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
        ( A ) ORGANISM: Escherichia coli ( x i ) SEQUENCE DESCRIPTION: SEQ ID NO:1:

```
Ser  Arg  Arg  Lys  Phe  Leu  Lys  Asp  Ile  Asn  Val  Gly  Ala  Gly  Leu  Pro
 1                  5                        10                            15

Val  Ile  Glu  Asn  Leu  Gln  Asn  Leu  Leu  Asn  Ala  Gly  Asp
                  20                       25
```

( 2 ) INFORMATION FOR SEQ ID NO:2:

( i ) SEQUENCE CHARACTERISTICS:
        ( A ) LENGTH: 29 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
        ( A ) ORGANISM: Escherichia coli ( x i ) SEQUENCE DESCRIPTION: SEQ ID NO:2:

```
Thr  Gly  Arg  His  Trp  Leu  Tyr  Asn  Ala  Thr  Val  Gly  Ala  Gly  Leu  Pro
 1                  5                        10                            15

Ile  Asn  His  Thr  Val  Arg  Asp  Leu  Ile  Asp  Ser  Gly  Asp
                  20                       25
```

( 2 ) INFORMATION FOR SEQ ID NO:3:

( i ) SEQUENCE CHARACTERISTICS:
        ( A ) LENGTH: 29 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
        ( A ) ORGANISM: Bacillus subtilis ( x i ) SEQUENCE DESCRIPTION: SEQ ID NO:3:

```
            Glu  Asn  Gly  Cys  Asp  Thr  Tyr  Phe  Glu  Ala  Ser  Val  Ala  Gly  Gly  Ile
             1                  5                       10                            15

Pro  Ile  Leu  Arg  Thr  Leu  Glu  Glu  Gly  Leu  Ser  Ser  Asp
                           20                       25
```

( 2 ) INFORMATION FOR SEQ ID NO:4:

( i ) SEQUENCE CHARACTERISTICS:
    ( A ) LENGTH: 27 amino acids
    ( B ) TYPE: amino acid
    ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
    ( A ) ORGANISM: Bacillus lactofermentum ( x i ) SEQUENCE DESCRIPTION: SEQ ID NO:4:

```
            Asn  Val  Asp  Leu  Tyr  Phe  Glu  Ala  Ala  Val  Ala  Gly  Ala  Leu  Pro  Val
             1                  5                       10                            15

Val  Gly  Pro  Leu  Arg  Arg  Ser  Leu  Ala  Gly  Asp
                           20                       25
```

( 2 ) INFORMATION FOR SEQ ID NO:5:

( i ) SEQUENCE CHARACTERISTICS:
    ( A ) LENGTH: 21 amino acids
    ( B ) TYPE: amino acid
    ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
    ( A ) ORGANISM: Daucus carota ( x i ) SEQUENCE DESCRIPTION: SEQ ID NO:5:

```
            Thr  Leu  Asp  Tyr  Gln  Glu  Ala  Trp  Glu  Met  Ser  Tyr  Phe  Gly  Ala  Asn
             1                  5                       10                            15

Val  Leu  His  Pro  Arg
                           20
```

( 2 ) INFORMATION FOR SEQ ID NO:6:

( i ) SEQUENCE CHARACTERISTICS:
    ( A ) LENGTH: 21 amino acids
    ( B ) TYPE: amino acid
    ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
    ( A ) ORGANISM: Escherichia coli ( x i ) SEQUENCE DESCRIPTION: SEQ ID NO:6:

```
            Ser  Met  Ser  Tyr  Gln  Glu  Ala  Met  Glu  Leu  Ser  Tyr  Phe  Gly  Ala  Lys
             1                  5                       10                            15

Val  Leu  His  Pro  Arg
```

20

(2) INFORMATION FOR SEQ ID NO:7:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: Escherichia coli (xi) SEQUENCE DESCRIPTION: SEQ ID NO:7:

Leu Leu Arg Leu Asp Glu Ala Ser Glu Leu Ala Arg Leu Ala Ala Pro
 1               5                  10                 15

Val Leu His Ala Arg
             20

(2) INFORMATION FOR SEQ ID NO:8:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: Escherichia coli (xi) SEQUENCE DESCRIPTION: SEQ ID NO:8:

Glu Ile Ala Phe Ala Glu Ala Ala Phe Met Ala Thr Phe Gly Ala Lys
 1               5                  10                 15

Val Leu His Pro Ala
             20

(2) INFORMATION FOR SEQ ID NO:9:

(i) SEQUENCE CHARACTERISTICS:
        (A) LENGTH: 21 amino acids
        (B) TYPE: amino acid
        (D) TOPOLOGY: linear (ii) MOLECULE TYPE: peptide (iii) HYPOTHETICAL: NO (v) FRAGMENT TYPE: internal (vi) ORIGINAL SOURCE:
        (A) ORGANISM: Bacillus subtilis (xi) SEQUENCE DESCRIPTION: SEQ ID NO:9:

Gly Ile Ser Tyr Asp Glu Met Leu Glu Leu Ala Asn Leu Gly Ala Gly
 1               5                  10                 15

Val Leu His Pro Arg
             20

(2) INFORMATION FOR SEQ ID NO:10:

( i ) SEQUENCE CHARACTERISTICS:
    ( A ) LENGTH: 21 amino acids
    ( B ) TYPE: amino acid
    ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
    ( A ) ORGANISM: Yeast ( x i ) SEQUENCE DESCRIPTION: SEQ ID NO:10:

```
Ser  Val  Thr  Pro  Glu  Glu  Ala  Ser  Glu  Leu  Thr  Tyr  Tyr  Gly  Ser  Glu
 1                   5                        10                        15
Val  Ile  His  Pro  Phe
                20
```

( 2 ) INFORMATION FOR SEQ ID NO:11:

( i ) SEQUENCE CHARACTERISTICS:
    ( A ) LENGTH: 23 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Daucus carota ( x i ) SEQUENCE DESCRIPTION: SEQ ID NO:11:

GCTTCATAAA AATAATGNGT ATA    23

( 2 ) INFORMATION FOR SEQ ID NO:12:

( i ) SEQUENCE CHARACTERISTICS:
    ( A ) LENGTH: 21 base pairs
    ( B ) TYPE: nucleic acid
    ( C ) STRANDEDNESS: single
    ( D ) TOPOLOGY: linear ( i i ) MOLECULE TYPE: DNA (genomic)

( i i i ) HYPOTHETICAL: NO ( v i ) ORIGINAL SOURCE:
    ( A ) ORGANISM: Daucus carota ( x i ) SEQUENCE DESCRIPTION: SEQ ID NO:12:

TATCAAGAAG CMTGGGAAAT G    21

( 2 ) INFORMATION FOR SEQ ID NO:13:

( i ) SEQUENCE CHARACTERISTICS:
    ( A ) LENGTH: 8 amino acids
    ( B ) TYPE: amino acid
    ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal (vi) ORIGINAL SOURCE:
    (A) ORGANISM: Daucus carota (xi) SEQUENCE DESCRIPTION: SEQ ID NO:13:

Tyr Gln Glu Ala Gln Trp Glu Met
 1               5

(2) INFORMATION FOR SEQ ID NO:14:

(i) SEQUENCE CHARACTERISTICS:
       (A) LENGTH: 23 base pairs
       (B) TYPE: nucleic acid
       (C) STRANDEDNESS: single
       (D) TOPOLOGY: linear (ii) MOLECULE TYPE: DNA (genomic)

(iii) HYPOTHETICAL: NO (iv) ANTI-SENSE: NO (vi) ORIGINAL SOURCE:
       (A) ORGANISM: Daucus carota (xi) SEQUENCE DESCRIPTION: SEQ ID NO:14:

GCTTCATAAA AATAATGNGT ATA    23

(2) INFORMATION FOR SEQ ID NO:15:

(i) SEQUENCE CHARACTERISTICS:
       (A) LENGTH: 8 amino acids
       (B) TYPE: amino acid
       (D) TOPOLOGY: linear (ii) MOLECULE TYPE: peptide (iii) HYPOTHETICAL: NO (v) FRAGMENT TYPE: internal (vi) ORIGINAL SOURCE:
       (A) ORGANISM: Daucus carota (xi) SEQUENCE DESCRIPTION: SEQ ID NO:15:

Tyr Thr His Tyr Phe Tyr Glu Ala
 1               5

(2) INFORMATION FOR SEQ ID NO:16:

(i) SEQUENCE CHARACTERISTICS:
       (A) LENGTH: 5 amino acids
       (B) TYPE: amino acid
       (D) TOPOLOGY: linear (ii) MOLECULE TYPE: peptide (iii) HYPOTHETICAL: NO (v) FRAGMENT TYPE: internal (vi) ORIGINAL SOURCE:
       (A) ORGANISM: Daucus carota (xi) SEQUENCE DESCRIPTION: SEQ ID NO:16:

Lys Phe Gly Gly Thr
 1               5

(2) INFORMATION FOR SEQ ID NO:17:

(i) SEQUENCE CHARACTERISTICS:
       (A) LENGTH: 5 amino acids
       (B) TYPE: amino acid (D) TOPOLOGY: linear (ii) MOLECULE TYPE: peptide (iii) HYPOTHETICAL: NO (v) FRAGMENT TYPE: internal (vi) ORIGINAL SOURCE:
    (A) ORGANISM: Daucus carota (xi) SEQUENCE DESCRIPTION: SEQ ID NO:17:

```
Lys  Phe  Gly  Gly  Ser
 1                    5
```

(2) INFORMATION FOR SEQ ID NO:18:

(i) SEQUENCE CHARACTERISTICS:
    (A) LENGTH: 2915 base pairs
    (B) TYPE: nucleic acid
    (C) STRANDEDNESS: single
    (D) TOPOLOGY: linear (ii) MOLECULE TYPE: DNA (genomic)

(iii) HYPOTHETICAL: NO (iv) ANTI-SENSE: NO (vi) ORIGINAL SOURCE:
    (A) ORGANISM: Daucus carota (ix) FEATURE:
    (A) NAME/KEY: CDS
    (B) LOCATION: 2..2593

(xi) SEQUENCE DESCRIPTION: SEQ ID NO:18:

```
G GAG TCG TCG TCG AAG TTT TAC ATT GCT GCT TCC GTT ACA ACT GCA                46
  Glu Ser Ser Ser Lys Phe Tyr Ile Ala Ala Ser Val Thr Thr Ala
   1           5                  10                 15

GTT CCT TCT CTC GAT GAC TCC GTT GAG AAG GTT CAC CTT CCC AGG GGT              94
Val Pro Ser Leu Asp Asp Ser Val Glu Lys Val His Leu Pro Arg Gly
                20              25                  30

GCT ATG TGG TCT ATT CAT AAA TTT GGA GGC ACC TGT GTG GGA AGC TCT             142
Ala Met Trp Ser Ile His Lys Phe Gly Gly Thr Cys Val Gly Ser Ser
            35                  40                  45

GAA AGG ATC CGA AAT GTT GCA GAG ATA GTT GTG GAG GAT GAT TCT GAA             190
Glu Arg Ile Arg Asn Val Ala Glu Ile Val Val Glu Asp Asp Ser Glu
        50                  55                  60

AGA AAG CTA GTT GTA GTC TCT GCA ATG TCA AAG GTC ACA GAT ATG ATG             238
Arg Lys Leu Val Val Val Ser Ala Met Ser Lys Val Thr Asp Met Met
    65                  70                  75

TAT GAT CTA ATT TAC AAG GCG CAG TCA CGG GAT GAT TCT TAT GAA TCT             286
Tyr Asp Leu Ile Tyr Lys Ala Gln Ser Arg Asp Asp Ser Tyr Glu Ser
 80                  85                  90                  95

GCG CTC GAT GCT GTT ATG GAA AAG CAC AAG TTA ACA GCA TTT GAT CTC             334
Ala Leu Asp Ala Val Met Glu Lys His Lys Leu Thr Ala Phe Asp Leu
                100                 105                 110

CTT GAT GGA GAT GAC CTT GCT AGA TTT TTA ACT AGG CTG CAA CAT GAT             382
Leu Asp Gly Asp Asp Leu Ala Arg Phe Leu Thr Arg Leu Gln His Asp
            115                 120                 125

GTT AAT AAC CTC AAA GCA ATG CTT CGT GCA ATA TAC ATA GCT GGT CAT             430
Val Asn Asn Leu Lys Ala Met Leu Arg Ala Ile Tyr Ile Ala Gly His
        130                 135                 140

GCC ACC GAA TCT TTT TCG GAT TTT GTT GTG GGA CAT GGA GAG CTA TGG             478
Ala Thr Glu Ser Phe Ser Asp Phe Val Val Gly His Gly Glu Leu Trp
    145                 150                 155
```

| | | | | | | | | | | | | | | | | |
|---|---|---|---|---|---|---|---|---|---|---|---|---|---|---|---|---|
| TCA | GCT | CAG | CTG | TTG | TCA | TTT | GTA | ATA | AGA | AAG | AAT | GGG | GGT | GAC | TGT | 526 |
| Ser | Ala | Gln | Leu | Leu | Ser | Phe | Val | Ile | Arg | Lys | Asn | Gly | Gly | Asp | Cys | |
| 160 | | | | | 165 | | | | | 170 | | | | | 175 | |
| AAT | TGG | ATG | GAC | ACA | CGA | GAT | GTT | CTT | GTT | GTA | AAT | CCT | GCT | GGA | TCT | 574 |
| Asn | Trp | Met | Asp | Thr | Arg | Asp | Val | Leu | Val | Val | Asn | Pro | Ala | Gly | Ser | |
| | | | | 180 | | | | | 185 | | | | | 190 | | |
| AAT | CAA | GTC | GAT | CCT | GAT | TAT | TTG | GAA | TCT | GAG | AAG | AGA | CTT | GAG | AAA | 622 |
| Asn | Gln | Val | Asp | Pro | Asp | Tyr | Leu | Glu | Ser | Glu | Lys | Arg | Leu | Glu | Lys | |
| | | | 195 | | | | | 200 | | | | | 205 | | | |
| TGG | TTC | TCC | AGC | AAC | CAG | TGT | CAG | ACA | ATT | GTT | GCG | ACA | GGT | TTT | ATA | 670 |
| Trp | Phe | Ser | Ser | Asn | Gln | Cys | Gln | Thr | Ile | Val | Ala | Thr | Gly | Phe | Ile | |
| | | 210 | | | | | 215 | | | | | 220 | | | | |
| GCT | AGC | ACG | CCT | CAA | AAT | ATA | CCT | ACA | ACT | TTG | AAA | AGA | GAC | GGA | AGT | 718 |
| Ala | Ser | Thr | Pro | Gln | Asn | Ile | Pro | Thr | Thr | Leu | Lys | Arg | Asp | Gly | Ser | |
| | 225 | | | | | 230 | | | | | 235 | | | | | |
| GAC | TTT | TCT | GCC | GCT | ATA | ATG | GGT | GCT | TTA | TTA | AGG | GCT | GGT | CAA | GTC | 766 |
| Asp | Phe | Ser | Ala | Ala | Ile | Met | Gly | Ala | Leu | Leu | Arg | Ala | Gly | Gln | Val | |
| 240 | | | | | 245 | | | | | 250 | | | | | 255 | |
| ACG | ATT | TGG | ACT | GAT | GTT | AAT | GGT | GTA | TAT | AGT | GCA | GAT | CCT | CGA | AAA | 814 |
| Thr | Ile | Trp | Thr | Asp | Val | Asn | Gly | Val | Tyr | Ser | Ala | Asp | Pro | Arg | Lys | |
| | | | | 260 | | | | | 265 | | | | | 270 | | |
| GTT | AGT | GAG | GCT | GTG | GTA | TTA | AAG | ACA | TTG | TCT | TAT | CAA | GAA | GCC | TGG | 862 |
| Val | Ser | Glu | Ala | Val | Val | Leu | Lys | Thr | Leu | Ser | Tyr | Gln | Glu | Ala | Trp | |
| | | | 275 | | | | | 280 | | | | | 285 | | | |
| GAG | ATG | TCA | TAT | TTT | GGG | GCT | AAT | GTG | TTA | CAT | CCC | CGT | ACT | ATC | ATT | 910 |
| Glu | Met | Ser | Tyr | Phe | Gly | Ala | Asn | Val | Leu | His | Pro | Arg | Thr | Ile | Ile | |
| | | 290 | | | | | 295 | | | | | 300 | | | | |
| CCT | GTG | ATG | CGA | TAT | GAC | ATT | CCA | ATT | GTA | ATA | AGA | AAT | ATA | TTC | AAC | 958 |
| Pro | Val | Met | Arg | Tyr | Asp | Ile | Pro | Ile | Val | Ile | Arg | Asn | Ile | Phe | Asn | |
| | 305 | | | | | 310 | | | | | 315 | | | | | |
| CTA | TCT | GCT | CCG | GGA | ACA | ATG | ATA | TGC | CGA | GAA | TCT | GTA | GGC | GAA | ACT | 1006 |
| Leu | Ser | Ala | Pro | Gly | Thr | Met | Ile | Cys | Arg | Glu | Ser | Val | Gly | Glu | Thr | |
| 320 | | | | | 325 | | | | | 330 | | | | | 335 | |
| GAA | GAT | GGG | TTA | AAA | TTG | GAA | TCT | CAT | GTC | AAA | GGA | TTT | GCT | ACT | ATT | 1054 |
| Glu | Asp | Gly | Leu | Lys | Leu | Glu | Ser | His | Val | Lys | Gly | Phe | Ala | Thr | Ile | |
| | | | | 340 | | | | | 345 | | | | | 350 | | |
| GAT | AAT | CTG | GCG | CTC | ATT | AAT | GTT | GAA | GGA | ACT | GGA | ATG | GCT | GGT | GTT | 1102 |
| Asp | Asn | Leu | Ala | Leu | Ile | Asn | Val | Glu | Gly | Thr | Gly | Met | Ala | Gly | Val | |
| | | | 355 | | | | | 360 | | | | | 365 | | | |
| CCT | GGT | ACA | GCT | AGT | GCA | ATT | TTT | GGT | GCT | GTC | AAG | GAT | GTG | GGA | GCT | 1150 |
| Pro | Gly | Thr | Ala | Ser | Ala | Ile | Phe | Gly | Ala | Val | Lys | Asp | Val | Gly | Ala | |
| | | 370 | | | | | 375 | | | | | 380 | | | | |
| AAT | GTT | ATA | ATG | ATA | TCT | CAG | GCT | AGC | AGT | GAG | CAT | TCT | ATT | TGC | TTT | 1198 |
| Asn | Val | Ile | Met | Ile | Ser | Gln | Ala | Ser | Ser | Glu | His | Ser | Ile | Cys | Phe | |
| | 385 | | | | | 390 | | | | | 395 | | | | | |
| GCT | GTG | CCT | GAG | AGT | GAA | GTG | AAA | GCT | GTT | GCT | AAA | GCT | TTG | GAG | GCC | 1246 |
| Ala | Val | Pro | Glu | Ser | Glu | Val | Lys | Ala | Val | Ala | Lys | Ala | Leu | Glu | Ala | |
| 400 | | | | | 405 | | | | | 410 | | | | | 415 | |
| AGA | TTT | CGT | CAA | GCT | TTA | GAT | GCT | AAT | CGT | CTT | TCC | CAG | GTT | GCT | ATT | 1294 |
| Arg | Phe | Arg | Gln | Ala | Leu | Asp | Ala | Asn | Arg | Leu | Ser | Gln | Val | Ala | Ile | |
| | | | | 420 | | | | | 425 | | | | | 430 | | |
| ATT | CCA | AAC | TGT | AGC | ATC | TTG | GCA | ACA | GTT | GGC | CAA | AAG | ATG | GCA | AGT | 1342 |
| Ile | Pro | Asn | Cys | Ser | Ile | Leu | Ala | Thr | Val | Gly | Gln | Lys | Met | Ala | Ser | |
| | | | 435 | | | | | 440 | | | | | 445 | | | |
| ACT | CCT | GGC | GTG | AGT | GCT | ACA | CTT | TTC | AAT | GCG | CTT | GCA | AAG | GCC | AAT | 1390 |
| Thr | Pro | Gly | Val | Ser | Ala | Thr | Leu | Phe | Asn | Ala | Leu | Ala | Lys | Ala | Asn | |
| | | | 450 | | | | | 455 | | | | | 460 | | | |
| ATA | AAC | GTT | CGT | GCT | ATA | GCC | CAG | GGC | TGT | ACA | GAG | TAT | AAT | ATC | ACT | 1438 |
| Ile | Asn | Val | Arg | Ala | Ile | Ala | Gln | Gly | Cys | Thr | Glu | Tyr | Asn | Ile | Thr | |
| | 465 | | | | | 470 | | | | | 475 | | | | | |

| | | | | | | | | | | | | | | | | |
|---|---|---|---|---|---|---|---|---|---|---|---|---|---|---|---|---|
| GTA | GTT | CTC | AGT | CGA | GAA | GAT | TGT | GTG | AGG | GCT | TTG | AAA | GCT | GTC | CAT | 1486 |
| Val | Val | Leu | Ser | Arg | Glu | Asp | Cys | Val | Arg | Ala | Leu | Lys | Ala | Val | His | |
| 480 | | | | 485 | | | | 490 | | | | | | | 495 | |
| TCA | AGA | TTT | TAT | CTG | TCG | AGA | ACC | ACA | ATA | GCA | GTG | GGT | ATT | GTC | GGA | 1534 |
| Ser | Arg | Phe | Tyr | Leu | Ser | Arg | Thr | Thr | Ile | Ala | Val | Gly | Ile | Val | Gly | |
| | | | | 500 | | | | 505 | | | | | 510 | | | |
| CCT | GGA | TTA | ATC | GGA | GCT | ACT | TTA | CTT | GAC | CAG | CTC | AGG | GAT | CAG | GCA | 1582 |
| Pro | Gly | Leu | Ile | Gly | Ala | Thr | Leu | Leu | Asp | Gln | Leu | Arg | Asp | Gln | Ala | |
| | | | 515 | | | | | 520 | | | | | 525 | | | |
| GCA | ATC | CTC | AAG | GAA | AAT | TCT | AAA | ATT | GAT | TTG | CGT | GTT | ATG | GGT | ATC | 1630 |
| Ala | Ile | Leu | Lys | Glu | Asn | Ser | Lys | Ile | Asp | Leu | Arg | Val | Met | Gly | Ile | |
| | | | 530 | | | | 535 | | | | | 540 | | | | |
| ACC | GGA | TCG | AGA | ACA | ATG | CTT | CTG | AGC | GAA | ACG | GGA | ATC | GAT | TTA | AGT | 1678 |
| Thr | Gly | Ser | Arg | Thr | Met | Leu | Leu | Ser | Glu | Thr | Gly | Ile | Asp | Leu | Ser | |
| | 545 | | | | | 550 | | | | | 555 | | | | | |
| AGA | TGG | AGA | GAA | GTC | CAA | AAA | GAG | AAA | GGG | CAA | ACA | GCT | GGC | CTA | GAA | 1726 |
| Arg | Trp | Arg | Glu | Val | Gln | Lys | Glu | Lys | Gly | Gln | Thr | Ala | Gly | Leu | Glu | |
| 560 | | | | | 565 | | | | | 570 | | | | | 575 | |
| AAA | TTT | GTA | CAA | CAT | GTG | CGT | GGA | AAT | CAT | TTT | ATT | CCA | AGC | ACT | GTT | 1774 |
| Lys | Phe | Val | Gln | His | Val | Arg | Gly | Asn | His | Phe | Ile | Pro | Ser | Thr | Val | |
| | | | | 580 | | | | 585 | | | | | | 590 | | |
| ATA | GTA | GAT | TGT | ACA | GCA | GAC | TCT | GAA | GTG | GCA | AGT | CAC | TAC | CAT | GAC | 1822 |
| Ile | Val | Asp | Cys | Thr | Ala | Asp | Ser | Glu | Val | Ala | Ser | His | Tyr | His | Asp | |
| | | | 595 | | | | 600 | | | | | 605 | | | | |
| TGG | TTG | TGT | AGG | GGA | ATT | CAC | TGC | ATT | ACC | CCA | AAT | AAG | AAG | GCA | AAT | 1870 |
| Trp | Leu | Cys | Arg | Gly | Ile | His | Cys | Ile | Thr | Pro | Asn | Lys | Lys | Ala | Asn | |
| | | 610 | | | | | 615 | | | | | 620 | | | | |
| TCA | GGA | CCC | CTT | GAT | CAG | TAT | TTG | AAG | TTG | AGA | GCT | CTC | CAG | CGG | CGA | 1918 |
| Ser | Gly | Pro | Leu | Asp | Gln | Tyr | Leu | Lys | Leu | Arg | Ala | Leu | Gln | Arg | Arg | |
| | 625 | | | | | 630 | | | | | 635 | | | | | |
| TCC | TAT | ACA | CAC | TAT | TTC | TAT | GAA | GCT | ACT | GTT | GGT | GCT | GGT | CTC | CCG | 1966 |
| Ser | Tyr | Thr | His | Tyr | Phe | Tyr | Glu | Ala | Thr | Val | Gly | Ala | Gly | Leu | Pro | |
| 640 | | | | | 645 | | | | | 650 | | | | | 655 | |
| ATC | ATA | ACC | ACT | TTG | CAG | GGA | CTT | CTT | GAA | ACC | GGG | GAC | AAG | ATA | TTG | 2014 |
| Ile | Ile | Thr | Thr | Leu | Gln | Gly | Leu | Leu | Glu | Thr | Gly | Asp | Lys | Ile | Leu | |
| | | | | 660 | | | | | 665 | | | | | 670 | | |
| CGA | ATT | GAA | GGC | ATT | TTC | AGT | GGG | ACT | CTT | AGT | TAC | ATA | TTC | AAC | AAC | 2062 |
| Arg | Ile | Glu | Gly | Ile | Phe | Ser | Gly | Thr | Leu | Ser | Tyr | Ile | Phe | Asn | Asn | |
| | | | | 675 | | | | 680 | | | | | 685 | | | |
| TTT | AAG | AGT | ACA | ACA | CCT | TTT | AGT | GAA | GTG | GTA | AGT | GAG | GCA | AAA | GCG | 2110 |
| Phe | Lys | Ser | Thr | Thr | Pro | Phe | Ser | Glu | Val | Val | Ser | Glu | Ala | Lys | Ala | |
| | | 690 | | | | | 695 | | | | | 700 | | | | |
| GCA | GGG | TAT | ACT | GAA | CCA | GAT | CCA | AGG | GAT | GAT | CTA | GCC | GGA | ACT | GAT | 2158 |
| Ala | Gly | Tyr | Thr | Glu | Pro | Asp | Pro | Arg | Asp | Asp | Leu | Ala | Gly | Thr | Asp | |
| | 705 | | | | | 710 | | | | | 715 | | | | | |
| GTT | GCT | AGA | AAG | GTA | ATA | ATT | CTT | GCT | AGA | GAA | TCT | GGA | TTA | AAG | CTC | 2206 |
| Val | Ala | Arg | Lys | Val | Ile | Ile | Leu | Ala | Arg | Glu | Ser | Gly | Leu | Lys | Leu | |
| 720 | | | | | 725 | | | | | 730 | | | | | 735 | |
| GAA | CTG | TCT | GAT | ATC | CCT | GTA | CAG | AGC | CTT | GTT | CCA | GAA | CCA | CTA | AGG | 2254 |
| Glu | Leu | Ser | Asp | Ile | Pro | Val | Gln | Ser | Leu | Val | Pro | Glu | Pro | Leu | Arg | |
| | | | | 740 | | | | | 745 | | | | | 750 | | |
| GGT | ATT | GCG | TCA | GCC | GAA | GAA | TTT | CTG | CTA | CAG | CTA | CCA | CAG | TTT | GAT | 2302 |
| Gly | Ile | Ala | Ser | Ala | Glu | Glu | Phe | Leu | Leu | Gln | Leu | Pro | Gln | Phe | Asp | |
| | | | 755 | | | | | 760 | | | | | 765 | | | |
| TCA | GAT | ATG | ACC | AGA | AAA | CGA | GAG | GAT | GCT | GAA | AAT | GCA | GGG | GAA | GTT | 2350 |
| Ser | Asp | Met | Thr | Arg | Lys | Arg | Glu | Asp | Ala | Glu | Asn | Ala | Gly | Glu | Val | |
| | | | 770 | | | | 775 | | | | | 780 | | | | |
| CTA | AGG | TAC | GTT | GGG | GTG | GTG | GAT | GCC | GTA | AAT | CAA | AAA | GGT | GTT | GTT | 2398 |
| Leu | Arg | Tyr | Val | Gly | Val | Val | Asp | Ala | Val | Asn | Gln | Lys | Gly | Val | Val | |
| 785 | | | | | 790 | | | | | 795 | | | | | | |

| | | | | | | | | | | | | | | | | |
|---|---|---|---|---|---|---|---|---|---|---|---|---|---|---|---|---|
| GAA | TTG | AAA | AGA | TAC | AAG | AAA | GAG | CAC | CCG | TTC | GCA | CAG | CTT | TCT | GGG | 2446 |
| Glu | Leu | Lys | Arg | Tyr | Lys | Lys | Glu | His | Pro | Phe | Ala | Gln | Leu | Ser | Gly | |
| 800 | | | | 805 | | | | 810 | | | | | | | 815 | |
| TCC | GAT | AAC | ATC | ATT | GCT | TTC | ACA | ACT | GAA | AGA | TAC | AAC | AAG | CAA | CCT | 2494 |
| Ser | Asp | Asn | Ile | Ile | Ala | Phe | Thr | Thr | Glu | Arg | Tyr | Asn | Lys | Gln | Pro | |
| | | | | 820 | | | | 825 | | | | | | 830 | | |
| CTT | ATA | ATT | CGA | GGT | CCT | GGT | GCT | GGG | GCA | GAG | GTG | ACA | GCT | GGT | GGA | 2542 |
| Leu | Ile | Ile | Arg | Gly | Pro | Gly | Ala | Gly | Ala | Glu | Val | Thr | Ala | Gly | Gly | |
| | | | 835 | | | | | 840 | | | | | 845 | | | |
| GTA | TTC | AGT | GAT | ATT | TTG | CGG | CTT | GCT | TCA | TAT | CTT | GGT | GCA | CCA | TCA | 2590 |
| Val | Phe | Ser | Asp | Ile | Leu | Arg | Leu | Ala | Ser | Tyr | Leu | Gly | Ala | Pro | Ser | |
| | | 850 | | | | | 855 | | | | | 860 | | | | |

```
TAATCCATTA GTTGAGCTCT CAATGTTTTA CCCTTTGTCA GCCCAAATTA TGTTATAGAA    2650
TTTAGGGAGC TTTTGCCTAT TATTAGGTTA GTATCAAAAC ATTCTTCTAC GCTGCATAAG    2710
AGAACACTTC ATGCAATTTG GGTTTCTTTA GTGGCTTTCT AGCCAACCCA AATGTGTCAT    2770
AGTCTCCACG ATGCAGAGTT GATAGAATTG TTACAAGGGG ATGTATTATA GAACCAAGCC    2830
AATTAAACGG TGTATCCTTA TTTGGTAAGG GATAACGTAT TAATAATGCC AAAGTGTTGT    2890
AACATCTTTT GTTGCGAATA AATTT                                          2915
```

( 2 ) INFORMATION FOR SEQ ID NO:19:

( i ) SEQUENCE CHARACTERISTICS:
        ( A ) LENGTH: 863 amino acids
        ( B ) TYPE: amino acid
        ( D ) TOPOLOGY: linear ( i i ) MOLECULE TYPE: protein ( x i ) SEQUENCE DESCRIPTION: SEQ ID NO:19:

```
Glu  Ser  Ser  Ser  Lys  Phe  Tyr  Ile  Ala  Ala  Ser  Val  Thr  Thr  Ala  Val
  1              5                        10                       15

Pro  Ser  Leu  Asp  Asp  Ser  Val  Glu  Lys  Val  His  Leu  Pro  Arg  Gly  Ala
               20                        25                       30

Met  Trp  Ser  Ile  His  Lys  Phe  Gly  Gly  Thr  Cys  Val  Gly  Ser  Ser  Glu
               35                        40                       45

Arg  Ile  Arg  Asn  Val  Ala  Glu  Ile  Val  Val  Glu  Asp  Ser  Glu  Arg
     50                        55                       60

Lys  Leu  Val  Val  Val  Ser  Ala  Met  Ser  Lys  Val  Thr  Asp  Met  Met  Tyr
 65                           70                       75                  80

Asp  Leu  Ile  Tyr  Lys  Ala  Gln  Ser  Arg  Asp  Asp  Ser  Tyr  Glu  Ser  Ala
                    85                        90                       95

Leu  Asp  Ala  Val  Met  Glu  Lys  His  Lys  Leu  Thr  Ala  Phe  Asp  Leu  Leu
              100                       105                      110

Asp  Gly  Asp  Asp  Leu  Ala  Arg  Phe  Leu  Thr  Arg  Leu  Gln  His  Asp  Val
         115                       120                      125

Asn  Asn  Leu  Lys  Ala  Met  Leu  Arg  Ala  Ile  Tyr  Ile  Ala  Gly  His  Ala
     130                       135                      140

Thr  Glu  Ser  Phe  Ser  Asp  Phe  Val  Val  Gly  His  Gly  Glu  Leu  Trp  Ser
145                      150                       155                      160

Ala  Gln  Leu  Leu  Ser  Phe  Val  Ile  Arg  Lys  Asn  Gly  Gly  Asp  Cys  Asn
                    165                       170                      175

Trp  Met  Asp  Thr  Arg  Asp  Val  Leu  Val  Asn  Pro  Ala  Gly  Ser  Asn
              180                       185                      190

Gln  Val  Asp  Pro  Asp  Tyr  Leu  Glu  Ser  Glu  Lys  Arg  Leu  Glu  Lys  Trp
         195                       200                      205

Phe  Ser  Ser  Asn  Gln  Cys  Gln  Thr  Ile  Val  Ala  Thr  Gly  Phe  Ile  Ala
```

-continued

|     |     |     |     |     | 210 |     |     |     |     | 215 |     |     |     |     | 220 |
| --- | --- | --- | --- | --- | --- | --- | --- | --- | --- | --- | --- | --- | --- | --- | --- |
| Ser 225 | Thr | Pro | Gln | Asn | Ile 230 | Pro | Thr | Thr | Leu | Lys 235 | Arg | Asp | Gly | Ser | Asp 240 |
| Phe | Ser | Ala | Ala | Ile 245 | Met | Gly | Ala | Leu | Leu 250 | Arg | Ala | Gly | Gln | Val 255 | Thr |
| Ile | Trp | Thr | Asp 260 | Val | Asn | Gly | Val | Tyr 265 | Ser | Ala | Asp | Pro | Arg 270 | Lys | Val |
| Ser | Glu | Ala 275 | Val | Val | Leu | Lys | Thr 280 | Leu | Ser | Tyr | Gln | Glu 285 | Ala | Trp | Glu |
| Met | Ser 290 | Tyr | Phe | Gly | Ala | Asn 295 | Val | Leu | His | Pro | Arg 300 | Thr | Ile | Ile | Pro |
| Val 305 | Met | Arg | Tyr | Asp | Ile 310 | Pro | Ile | Val | Ile | Arg 315 | Asn | Ile | Phe | Asn | Leu 320 |
| Ser | Ala | Pro | Gly | Thr 325 | Met | Ile | Cys | Arg | Glu 330 | Ser | Val | Gly | Glu | Thr 335 | Glu |
| Asp | Gly | Leu | Lys 340 | Leu | Glu | Ser | His | Val 345 | Lys | Gly | Phe | Ala | Thr 350 | Ile | Asp |
| Asn | Leu | Ala 355 | Leu | Ile | Asn | Val | Glu 360 | Gly | Thr | Gly | Met | Ala 365 | Gly | Val | Pro |
| Gly | Thr 370 | Ala | Ser | Ala | Ile | Phe 375 | Gly | Ala | Val | Lys | Asp 380 | Val | Gly | Ala | Asn |
| Val 385 | Ile | Met | Ile | Ser | Gln 390 | Ala | Ser | Ser | Glu | His 395 | Ser | Ile | Cys | Phe | Ala 400 |
| Val | Pro | Glu | Ser | Glu 405 | Val | Lys | Ala | Val | Ala 410 | Lys | Ala | Leu | Glu | Ala 415 | Arg |
| Phe | Arg | Gln | Ala 420 | Leu | Asp | Ala | Asn | Arg 425 | Leu | Ser | Gln | Val | Ala 430 | Ile | Ile |
| Pro | Asn | Cys 435 | Ser | Ile | Leu | Ala | Thr 440 | Val | Gly | Gln | Lys | Met 445 | Ala | Ser | Thr |
| Pro | Gly 450 | Val | Ser | Ala | Thr | Leu 455 | Phe | Asn | Ala | Leu | Ala 460 | Lys | Ala | Asn | Ile |
| Asn 465 | Val | Arg | Ala | Ile | Ala 470 | Gln | Gly | Cys | Thr | Glu 475 | Tyr | Asn | Ile | Thr | Val 480 |
| Val | Leu | Ser | Arg | Glu 485 | Asp | Cys | Val | Arg | Ala 490 | Leu | Lys | Ala | Val | His 495 | Ser |
| Arg | Phe | Tyr | Leu 500 | Ser | Arg | Thr | Thr | Ile 505 | Ala | Val | Gly | Ile | Val 510 | Gly | Pro |
| Gly | Leu | Ile 515 | Gly | Ala | Thr | Leu | Leu 520 | Asp | Gln | Leu | Arg | Gln 525 | Ala | Ala |
| Ile | Leu | Lys 530 | Glu | Asn | Ser | Lys | Ile 535 | Asp | Leu | Arg | Val | Met 540 | Gly | Ile | Thr |
| Gly 545 | Ser | Arg | Thr | Met | Leu 550 | Leu | Ser | Glu | Thr | Gly 555 | Ile | Asp | Leu | Ser | Arg 560 |
| Trp | Arg | Glu | Val | Gln 565 | Lys | Glu | Lys | Gly | Gln 570 | Thr | Ala | Gly | Leu | Glu 575 | Lys |
| Phe | Val | Gln | His 580 | Val | Arg | Gly | Asn | His 585 | Phe | Ile | Pro | Ser | Thr 590 | Val | Ile |
| Val | Asp | Cys 595 | Thr | Ala | Asp | Ser | Glu 600 | Val | Ala | Ser | His | Tyr 605 | His | Asp | Trp |
| Leu | Cys | Arg 610 | Gly | Ile | His | Cys | Ile 615 | Thr | Pro | Asn | Lys 620 | Lys | Ala | Asn | Ser |
| Gly 625 | Pro | Leu | Asp | Gln | Tyr 630 | Leu | Lys | Leu | Arg | Ala 635 | Leu | Gln | Arg | Arg | Ser 640 |

```
Tyr  Thr  His  Tyr  Phe  Tyr  Glu  Ala  Thr  Val  Gly  Ala  Gly  Leu  Pro  Ile
               645                    650                         655

Ile  Thr  Thr  Leu  Gln  Gly  Leu  Leu  Glu  Thr  Gly  Asp  Lys  Ile  Leu  Arg
               660                    665                         670

Ile  Glu  Gly  Ile  Phe  Ser  Gly  Thr  Leu  Ser  Tyr  Ile  Phe  Asn  Asn  Phe
          675                    680                         685

Lys  Ser  Thr  Thr  Pro  Phe  Ser  Glu  Val  Val  Ser  Glu  Ala  Lys  Ala  Ala
     690                    695                         700

Gly  Tyr  Thr  Glu  Pro  Asp  Pro  Arg  Asp  Asp  Leu  Ala  Gly  Thr  Asp  Val
705                      710                    715                         720

Ala  Arg  Lys  Val  Ile  Ile  Leu  Ala  Arg  Glu  Ser  Gly  Leu  Lys  Leu  Glu
               725                    730                         735

Leu  Ser  Asp  Ile  Pro  Val  Gln  Ser  Leu  Val  Pro  Glu  Pro  Leu  Arg  Gly
               740                    745                         750

Ile  Ala  Ser  Ala  Glu  Glu  Phe  Leu  Leu  Gln  Leu  Pro  Gln  Phe  Asp  Ser
               755                    760                         765

Asp  Met  Thr  Arg  Lys  Arg  Glu  Asp  Ala  Glu  Asn  Ala  Gly  Glu  Val  Leu
     770                    775                         780

Arg  Tyr  Val  Gly  Val  Val  Asp  Ala  Val  Asn  Gln  Lys  Gly  Val  Val  Glu
785                      790                    795                         800

Leu  Lys  Arg  Tyr  Lys  Lys  Glu  His  Pro  Phe  Ala  Gln  Leu  Ser  Gly  Ser
               805                    810                         815

Asp  Asn  Ile  Ile  Ala  Phe  Thr  Thr  Glu  Arg  Tyr  Asn  Lys  Gln  Pro  Leu
               820                    825                         830

Ile  Ile  Arg  Gly  Pro  Gly  Ala  Gly  Ala  Glu  Val  Thr  Ala  Gly  Gly  Val
               835                    840                         845

Phe  Ser  Asp  Ile  Leu  Arg  Leu  Ala  Ser  Tyr  Leu  Gly  Ala  Pro  Ser
     850                    855                         860
```

( 2 ) INFORMATION FOR SEQ ID NO:20:

( i ) SEQUENCE CHARACTERISTICS:
        ( A ) LENGTH: 863 amino acids
        ( B ) TYPE: amino acid
        ( D ) TOPOLOGY: linear ( i i ) MOLECULE TYPE: protein ( i i i ) HYPOTHETICAL: NO ( v ) FRAGMENT TYPE: N-terminal ( v i ) ORIGINAL SOURCE:
        ( A ) ORGANISM: Daucus carota ( x i ) SEQUENCE DESCRIPTION: SEQ ID NO:20:

```
Glu  Ser  Ser  Ser  Lys  Phe  Tyr  Ile  Ala  Ala  Ser  Val  Thr  Thr  Ala  Val
 1              5                    10                         15

Pro  Ser  Leu  Asp  Asp  Ser  Val  Glu  Lys  Val  His  Leu  Pro  Arg  Gly  Ala
               20                    25                         30

Met  Trp  Ser  Ile  His  Lys  Phe  Gly  Gly  Thr  Cys  Val  Gly  Ser  Ser  Glu
               35                    40                         45

Arg  Ile  Arg  Asn  Val  Ala  Glu  Ile  Val  Val  Glu  Asp  Asp  Ser  Glu  Arg
          50                    55                         60

Lys  Leu  Val  Val  Val  Ser  Ala  Met  Ser  Lys  Val  Thr  Asp  Met  Met  Tyr
 65                      70                    75                         80

Asp  Leu  Ile  Tyr  Lys  Ala  Gln  Ser  Arg  Asp  Asp  Ser  Tyr  Glu  Ser  Ala
               85                    90                         95

Leu  Asp  Ala  Val  Met  Glu  Lys  His  Lys  Leu  Thr  Ala  Phe  Asp  Leu  Leu
```

-continued

|   |   |   | 100 |   |   |   | 105 |   |   |   | 110 |   |   |
|---|---|---|---|---|---|---|---|---|---|---|---|---|---|

Asp Gly Asp Asp Leu Ala Arg Phe Leu Thr Arg Leu Gln His Asp Val
        115                 120                 125

Asn Asn Leu Lys Ala Met Leu Arg Ala Ile Tyr Ile Ala Gly His Ala
130                 135                 140

Thr Glu Ser Phe Ser Asp Phe Val Val Gly His Gly Glu Leu Trp Ser
145                 150                 155                 160

Ala Gln Leu Leu Ser Phe Val Ile Arg Lys Asn Gly Gly Asp Cys Asn
                    165                 170                 175

Trp Met Asp Thr Arg Asp Val Leu Val Asn Pro Ala Gly Ser Asn
                180                 185                 190

Gln Val Asp Pro Asp Tyr Leu Glu Ser Glu Lys Arg Leu Glu Lys Trp
            195                 200                 205

Phe Ser Ser Asn Gln Cys Gln Thr Ile Val Ala Thr Gly Phe Ile Ala
210                 215                 220

Ser Thr Pro Gln Asn Ile Pro Thr Thr Leu Lys Arg Asp Gly Ser Asp
225                 230                 235                 240

Phe Ser Ala Ala Ile Met Gly Ala Leu Leu Arg Ala Gly Gln Val Thr
                245                 250                 255

Ile Trp Thr Asp Val Asn Gly Val Tyr Ser Ala Asp Pro Arg Lys Val
            260                 265                 270

Ser Glu Ala Val Val Leu Lys Thr Leu Ser Tyr Gln Glu Ala Trp Glu
        275                 280                 285

Met Ser Tyr Phe Gly Ala Asn Val Leu His Pro Arg Thr Ile Ile Pro
        290                 295                 300

Val Met Arg Tyr Asp Ile Pro Ile Val Ile Arg Asn Ile Phe Asn Leu
305                 310                 315                 320

Ser Ala Pro Gly Thr Met Ile Cys Arg Glu Ser Val Gly Glu Thr Glu
                325                 330                 335

Asp Gly Leu Lys Leu Glu Ser His Val Lys Gly Phe Ala Thr Ile Asp
            340                 345                 350

Asn Leu Ala Leu Ile Asn Val Glu Gly Thr Gly Met Ala Gly Val Pro
        355                 360                 365

Gly Thr Ala Ser Ala Ile Phe Gly Ala Val Lys Asp Val Gly Ala Asn
370                 375                 380

Val Ile Met Ile Ser Gln Ala Ser Ser Glu His Ser Ile Cys Phe Ala
385                 390                 395                 400

Val Pro Glu Ser Glu Val Lys Ala Val Ala Lys Ala Leu Glu Ala Arg
                405                 410                 415

Phe Arg Gln Ala Leu Asp Ala Gly Arg Leu Ser Gln Val Ala Ile Ile
            420                 425                 430

Pro Asn Cys Ser Ile Leu Ala Thr Val Gly Gln Lys Met Ala Ser Thr
        435                 440                 445

Pro Gly Val Ser Ala Thr Leu Phe Asn Ala Leu Ala Lys Ala Asn Ile
    450                 455                 460

Asn Val Arg Ala Ile Ala Gln Gly Cys Thr Glu Tyr Asn Ile Thr Val
465                 470                 475                 480

Val Leu Ser Arg Glu Asp Cys Val Arg Ala Leu Lys Ala Val His Ser
                485                 490                 495

Arg Phe Tyr Leu Ser Arg Thr Thr Ile Ala Val Gly Ile Val Gly Pro
            500                 505                 510

Gly Leu Ile Gly Ala Thr Leu Leu Asp Gln Leu Arg Asp Gln Ala Ala
        515                 520                 525

```
Ile  Leu  Lys  Glu  Asn  Ser  Lys  Ile  Asp  Leu  Arg  Val  Met  Gly  Ile  Thr
     530                 535                     540

Gly  Ser  Arg  Thr  Met  Leu  Leu  Ser  Glu  Thr  Gly  Ile  Asp  Leu  Ser  Arg
545                      550                     555                      560

Trp  Arg  Glu  Val  Gln  Lys  Glu  Lys  Gly  Gln  Thr  Ala  Gly  Leu  Glu  Lys
                    565                      570                      575

Phe  Val  Gln  His  Val  Arg  Gly  Asn  His  Phe  Ile  Pro  Ser  Thr  Val  Ile
               580                      585                     590

Val  Asp  Cys  Thr  Ala  Asp  Ser  Glu  Val  Ala  Ser  His  Tyr  His  Asp  Trp
          595                      600                     605

Leu  Cys  Arg  Gly  Ile  His  Val  Ile  Thr  Pro  Asn  Lys  Lys  Ala  Asn  Ser
     610                      615                     620

Gly  Pro  Leu  Asp  Gln  Tyr  Leu  Lys  Leu  Arg  Ala  Leu  Gln  Arg  Arg  Ser
625                      630                     635                      640

Tyr  Thr  His  Tyr  Phe  Tyr  Glu  Ala  Thr  Val  Gly  Ala  Gly  Leu  Pro  Ile
                    645                     650                      655

Ile  Thr  Thr  Leu  Gln  Gly  Leu  Leu  Glu  Thr  Gly  Asp  Lys  Ile  Leu  Arg
               660                     665                      670

Ile  Glu  Gly  Ile  Phe  Ser  Gly  Thr  Leu  Ser  Tyr  Ile  Phe  Asn  Asn  Phe
          675                     680                      685

Lys  Ser  Thr  Thr  Pro  Phe  Ser  Glu  Val  Val  Ser  Glu  Ala  Lys  Ala  Ala
     690                     695                      700

Gly  Tyr  Thr  Glu  Pro  Asp  Pro  Arg  Asp  Asp  Leu  Ala  Gly  Thr  Asp  Val
705                     710                      715                      720

Ala  Arg  Lys  Val  Ile  Ile  Leu  Ala  Arg  Glu  Ser  Gly  Leu  Lys  Leu  Glu
                    725                     730                      735

Leu  Ser  Asp  Ile  Pro  Val  Gln  Ser  Leu  Val  Pro  Glu  Pro  Leu  Arg  Gly
               740                     745                      750

Ile  Ala  Ser  Ala  Glu  Glu  Phe  Leu  Leu  Gln  Leu  Pro  Gln  Phe  Asp  Ser
          755                     760                      765

Asp  Met  Thr  Arg  Lys  Arg  Glu  Asp  Ala  Glu  Asn  Ala  Gly  Glu  Val  Leu
     770                     775                      780

Arg  Tyr  Val  Gly  Val  Val  Asp  Ala  Val  Asn  Gln  Lys  Gly  Val  Val  Glu
785                     790                      795                      800

Leu  Lys  Arg  Tyr  Lys  Lys  Glu  His  Pro  Phe  Ala  Gln  Leu  Ser  Gly  Ser
                    805                     810                      815

Asp  Asn  Ile  Ile  Ala  Phe  Thr  Thr  Glu  Arg  Tyr  Asn  Lys  Gln  Pro  Leu
               820                     825                      830

Ile  Ile  Arg  Gly  Pro  Gly  Ala  Gly  Ala  Glu  Val  Thr  Ala  Gly  Gly  Val
          835                     840                      845

Phe  Ser  Asp  Ile  Leu  Arg  Leu  Ala  Ser  Tyr  Leu  Gly  Ala  Pro  Ser
850                     855                      860
```

( 2 ) INFORMATION FOR SEQ ID NO:21:

( i ) SEQUENCE CHARACTERISTICS:
        ( A ) LENGTH: 33 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
        ( A ) ORGANISM: Daucus carota ( x i ) SEQUENCE DESCRIPTION: SEQ ID NO:21:

| Gly | Phe | Ala | Thr | Ile | Asp | Asn | Leu | Ala | Leu | Ile | Asn | Val | Glu | Gly | Thr |
| --- | --- | --- | --- | --- | --- | --- | --- | --- | --- | --- | --- | --- | --- | --- | --- |
| 1 | | | | 5 | | | | | 10 | | | | | 15 | |

| Gly | Met | Ala | Gly | Val | Pro | Gly | Thr | Ala | Ser | Ala | Ile | Phe | Ser | Ala | Val |
| --- | --- | --- | --- | --- | --- | --- | --- | --- | --- | --- | --- | --- | --- | --- | --- |
| | | | 20 | | | | 25 | | | | | 30 | | | |

Lys ( 2 ) INFORMATION FOR SEQ ID NO:22:

( i ) SEQUENCE CHARACTERISTICS:
        ( A ) LENGTH: 9 amino acids
        ( B ) TYPE: amino acid
        ( D ) TOPOLOGY: linear ( i i ) MOLECULE TYPE: peptide ( i i i ) HYPOTHETICAL: NO ( v ) FRAGMENT TYPE: internal ( v i ) ORIGINAL SOURCE:
        ( A ) ORGANISM: Daucus carota ( x i ) SEQUENCE DESCRIPTION: SEQ ID NO:22:

| Leu | Ala | Ser | Tyr | Leu | Gly | Ala | Pro | Ser |
| --- | --- | --- | --- | --- | --- | --- | --- | --- |
| 1 | | | | 5 | | | | |

( 2 ) INFORMATION FOR SEQ ID NO:23:

( i ) SEQUENCE CHARACTERISTICS:
        ( A ) LENGTH: 820 amino acids
        ( B ) TYPE: amino acid
        ( D ) TOPOLOGY: linear ( i i ) MOLECULE TYPE: protein ( i i i ) HYPOTHETICAL: NO ( v ) FRAGMENT TYPE: internal ( v i ) ORIGINAL SOURCE:
        ( A ) ORGANISM: Escherichia coli ( x i ) SEQUENCE DESCRIPTION: SEQ ID NO:23:

| Met | Arg | Val | Leu | Lys | Phe | Gly | Gly | Thr | Ser | Val | Ala | Asn | Ala | Glu | Arg |
| --- | --- | --- | --- | --- | --- | --- | --- | --- | --- | --- | --- | --- | --- | --- | --- |
| 1 | | | | 5 | | | | | 10 | | | | | 15 | |

| Phe | Leu | Arg | Val | Ala | Asp | Ile | Leu | Glu | Ser | Asn | Ala | Arg | Gln | Gly | Gln |
| --- | --- | --- | --- | --- | --- | --- | --- | --- | --- | --- | --- | --- | --- | --- | --- |
| | | | 20 | | | | | 25 | | | | | 30 | | |

| Val | Ala | Thr | Val | Leu | Ser | Ala | Pro | Ala | Lys | Ile | Thr | Asn | His | Leu | Val |
| --- | --- | --- | --- | --- | --- | --- | --- | --- | --- | --- | --- | --- | --- | --- | --- |
| | | 35 | | | | | 40 | | | | | 45 | | | |

| Ala | Met | Ile | Glu | Lys | Thr | Ile | Ser | Gly | Gln | Asp | Ala | Leu | Pro | Asn | Ile |
| --- | --- | --- | --- | --- | --- | --- | --- | --- | --- | --- | --- | --- | --- | --- | --- |
| | 50 | | | | | 55 | | | | | 60 | | | | |

| Ser | Asp | Ala | Glu | Arg | Ile | Phe | Ala | Glu | Leu | Leu | Thr | Gly | Leu | Ala | Ala |
| --- | --- | --- | --- | --- | --- | --- | --- | --- | --- | --- | --- | --- | --- | --- | --- |
| 65 | | | | | 70 | | | | | 75 | | | | | 80 |

| Ala | Gln | Pro | Gly | Phe | Pro | Leu | Ala | Gln | Leu | Lys | Thr | Phe | Val | Asp | Gln |
| --- | --- | --- | --- | --- | --- | --- | --- | --- | --- | --- | --- | --- | --- | --- | --- |
| | | | | 85 | | | | | 90 | | | | | 95 | |

| Glu | Phe | Ala | Gln | Ile | Lys | His | Val | Leu | His | Gly | Ile | Ser | Leu | Leu | Gly |
| --- | --- | --- | --- | --- | --- | --- | --- | --- | --- | --- | --- | --- | --- | --- | --- |
| | | | | 100 | | | | | 105 | | | | | 110 | |

| Gln | Cys | Pro | Asp | Ser | Ile | Asn | Ala | Ala | Leu | Ile | Cys | Arg | Gly | Glu | Lys |
| --- | --- | --- | --- | --- | --- | --- | --- | --- | --- | --- | --- | --- | --- | --- | --- |
| | | | 115 | | | | | 120 | | | | | 125 | | |

| Met | Ser | Ile | Ala | Ile | Met | Ala | Gly | Val | Leu | Glu | Ala | Arg | Gly | His | Asn |
| --- | --- | --- | --- | --- | --- | --- | --- | --- | --- | --- | --- | --- | --- | --- | --- |
| | | 130 | | | | | 135 | | | | | 140 | | | |

| Val | Thr | Val | Ile | Asp | Pro | Val | Glu | Lys | Leu | Leu | Ala | Val | Gly | His | Tyr |
| --- | --- | --- | --- | --- | --- | --- | --- | --- | --- | --- | --- | --- | --- | --- | --- |
| 145 | | | | | 150 | | | | | 155 | | | | | 160 |

```
Leu  Glu  Ser  Thr  Val  Asp  Ile  Ala  Glu  Ser  Thr  Arg  Arg  Ile  Ala  Ala
                    165                      170                     175

Ser  Arg  Ile  Pro  Ala  Asp  His  Met  Val  Leu  Met  Ala  Gly  Phe  Thr  Ala
                    180                      185                     190

Gly  Asn  Glu  Lys  Gly  Glu  Leu  Val  Val  Leu  Gly  Arg  Asn  Gly  Ser  Asp
               195                      200                 205

Tyr  Ser  Ala  Ala  Val  Leu  Ala  Ala  Cys  Leu  Arg  Ala  Asp  Cys  Cys  Glu
          210                      215                     220

Ile  Trp  Thr  Asp  Val  Asn  Gly  Val  Tyr  Thr  Cys  Asp  Pro  Arg  Gln  Val
225                      230                     235                          240

Pro  Asp  Ala  Arg  Leu  Leu  Lys  Ser  Met  Ser  Tyr  Gln  Glu  Ala  Met  Glu
                    245                      250                          255

Leu  Ser  Tyr  Phe  Gly  Ala  Lys  Val  Leu  His  Pro  Arg  Thr  Ile  Thr  Pro
               260                      265                     270

Ile  Ala  Gln  Phe  Gln  Ile  Pro  Cys  Leu  Ile  Lys  Asn  Thr  Gly  Asn  Pro
               275                      280                     285

Gln  Ala  Pro  Gly  Thr  Leu  Ile  Gly  Ala  Ser  Arg  Asp  Glu  Asp  Glu  Leu
          290                      295                     300

Pro  Val  Lys  Gly  Ile  Ser  Asn  Leu  Asn  Asn  Met  Ala  Met  Phe  Ser  Val
305                      310                     315                          320

Ser  Gly  Pro  Gly  Met  Lys  Gly  Met  Val  Gly  Met  Ala  Ala  Arg  Val  Phe
                    325                      330                          335

Ala  Ala  Met  Ser  Arg  Ala  Arg  Ile  Ser  Val  Val  Leu  Ile  Thr  Gln  Ser
               340                      345                     350

Ser  Ser  Glu  Tyr  Ser  Ile  Ser  Phe  Cys  Val  Pro  Gln  Ser  Asp  Cys  Val
          355                      360                     365

Arg  Ala  Glu  Arg  Ala  Met  Leu  Glu  Glu  Phe  Tyr  Leu  Glu  Leu  Lys  Glu
     370                      375                     380

Gly  Leu  Leu  Glu  Pro  Leu  Ala  Val  Ala  Glu  Arg  Leu  Ala  Ile  Ile  Ser
385                      390                     395                          400

Val  Val  Gly  Asp  Gly  Leu  Arg  Thr  Leu  Arg  Gly  Ile  Ser  Ala  Lys  Phe
                    405                      410                          415

Phe  Ala  Ala  Leu  Ala  Arg  Ala  Asn  Ile  Asn  Ile  Val  Ala  Ile  Ala  Gln
               420                      425                     430

Gly  Ser  Ser  Glu  Arg  Ser  Ile  Ser  Val  Val  Val  Asn  Asn  Asp  Asp  Ala
          435                      440                     445

Thr  Thr  Gly  Val  Arg  Val  Thr  His  Gln  Met  Leu  Phe  Asn  Thr  Asp  Gln
     450                      455                     460

Val  Ile  Glu  Val  Phe  Val  Ile  Gly  Val  Gly  Gly  Val  Gly  Gly  Ala  Leu
465                      470                     475                          480

Leu  Glu  Gln  Leu  Lys  Arg  Gln  Gln  Ser  Trp  Leu  Lys  Asn  Lys  His  Ile
                    485                      490                          495

Asp  Leu  Arg  Val  Cys  Gly  Val  Ala  Asn  Ser  Lys  Ala  Leu  Leu  Thr  Asn
               500                      505                     510

Val  His  Gly  Leu  Asn  Leu  Glu  Asn  Trp  Gln  Glu  Glu  Leu  Ala  Gln  Ala
     515                      520                     525

Lys  Glu  Pro  Phe  Asn  Leu  Gly  Arg  Leu  Ile  Arg  Leu  Val  Lys  Glu  Tyr
     530                      535                     540

His  Leu  Leu  Asn  Pro  Val  Ile  Val  Asn  Cys  Thr  Ser  Ser  Gln  Ala  Val
545                      550                     555                          560

Ala  Asp  Gln  Tyr  Ala  Asp  Phe  Leu  Arg  Glu  Gly  Phe  His  Val  Val  Thr
               565                      570                     575

Pro  Asn  Lys  Lys  Ala  Asn  Thr  Ser  Ser  Met  Asp  Tyr  Tyr  His  Gln  Leu
```

```
                         580                              585                              590
     Arg   Tyr   Ala   Ala   Glu   Lys   Ser   Arg   Arg   Lys   Phe   Leu   Tyr   Asp   Ile   Asn
                 595                           600                           605

Val   Gly   Ala   Gly   Leu   Pro   Val   Ile   Glu   Asn   Leu   Gln   Asn   Leu   Leu   Asn
           610                           615                           620

Ala   Gly   Asp   Glu   Leu   Met   Lys   Phe   Ser   Gly   Ile   Leu   Ser   Gly   Ser   Leu
     625                           630                           635                           640

Ser   Tyr   Ile   Phe   Gly   Lys   Leu   Asp   Glu   Gly   Met   Ser   Phe   Ser   Glu   Ala
                             645                           650                                 655

Thr   Arg   Leu   Ala   Arg   Glu   Met   Gly   Tyr   Thr   Glu   Pro   Asp   Pro   Arg   Asp
                 660                           665                           670

Asp   Leu   Ser   Gly   Met   Asp   Val   Ala   Arg   Lys   Leu   Leu   Ile   Leu   Ala   Arg
                 675                           680                           685

Glu   Thr   Gly   Arg   Glu   Leu   Glu   Leu   Ala   Asp   Ile   Glu   Ile   Glu   Pro   Val
           690                           695                           700

Leu   Pro   Ala   Glu   Phe   Asn   Ala   Glu   Gly   Asp   Val   Ala   Ala   Phe   Met   Ala
     705                           710                           715                           720

Asn   Leu   Ser   Gln   Leu   Asp   Asp   Leu   Phe   Ala   Ala   Arg   Val   Ala   Lys   Ala
                             725                           730                           735

Arg   Asp   Glu   Gly   Lys   Val   Leu   Arg   Tyr   Val   Gly   Asn   Ile   Asp   Glu   Asp
                       740                           745                           750

Gly   Val   Cys   Arg   Val   Lys   Ile   Ala   Glu   Val   Asp   Gly   Asn   Asp   Pro   Leu
                 755                           760                           765

Phe   Lys   Val   Lys   Asn   Gly   Glu   Asn   Ala   Leu   Ala   Phe   Tyr   Ser   His   Tyr
           770                           775                           780

Tyr   Gln   Pro   Leu   Pro   Leu   Val   Leu   Arg   Gly   Tyr   Gly   Ala   Gly   Asn   Asp
     785                           790                           795                           800

Val   Thr   Ala   Ala   Gly   Val   Phe   Ala   Asp   Leu   Leu   Arg   Thr   Leu   Ser   Trp
                       805                           810                           815

Lys   Leu   Gly   Val
                       820
```